US010922996B2

(12) United States Patent
Baharav et al.

(10) Patent No.: US 10,922,996 B2
(45) Date of Patent: Feb. 16, 2021

(54) SYSTEMS AND METHODS FOR GENERATING A PRESENTATION OF AN ENERGY LEVEL BASED ON SLEEP AND DAILY ACTIVITY

(71) Applicant: HypnoCore Ltd., Petach-Tikva (IL)

(72) Inventors: Armanda Lia Baharav, Tel-Aviv (IL); Shulamit Eyal, Givat Shmuel (IL); Hagit Liran, Beit-YeHoshua (IL)

(73) Assignee: HypnoCore Ltd., Petach-Tikva (IL)

( * ) Notice: Subject to any disclaimer, the term of this patent is extended or adjusted under 35 U.S.C. 154(b) by 266 days.

(21) Appl. No.: 15/893,866

(22) Filed: Feb. 12, 2018

(65) Prior Publication Data

US 2019/0251858 A1 Aug. 15, 2019

(51) Int. Cl.
*A61B 5/00* (2006.01)
*G09B 19/00* (2006.01)
(Continued)

(52) U.S. Cl.
CPC .......... *G09B 19/00* (2013.01); *A61B 5/02055* (2013.01); *A61B 5/1118* (2013.01); *A61B 5/18* (2013.01); *A61B 5/4812* (2013.01); *A61B 5/4815* (2013.01); *A61B 5/742* (2013.01); *A63B 24/0003* (2013.01); *A63B 24/0062* (2013.01);
(Continued)

(58) Field of Classification Search
CPC .......... A61B 5/00; A61B 5/48; A61B 5/4806; A61B 5/4809; A61B 5/4812; A61B 5/4815; A61B 5/74; A61B 5/42; A61B 5/7425; A61B 5/16; A61B 5/161; A61B 5/162;
(Continued)

(56) References Cited

U.S. PATENT DOCUMENTS 7,623,912 B2 * 11/2009 Akselrod ........... A61B 5/02405
600/513
8,112,149 B2 * 2/2012 Sholder ................ A61B 5/0006
600/515
(Continued)

OTHER PUBLICATIONS

Di Nuzzo et al., "Brain Energetics During the Sleep-Wake Cycle," Curr Opin Neurobiol. Author manuscript; available in PMC Dec. 16, 2017.*
(Continued)

*Primary Examiner* — Ahmed M Farah

(57) ABSTRACT

There is provided a method of creating a presentation of a current awake-energy level, comprising: computing an estimate of initial awake-energy at a wake-up time of a target individual according to sleep-parameters computed according to a time interval that includes a previous night sleep, computing an estimate of a current awake-energy of the target individual indicative of a remaining amount of an estimated maximal amount of available awake-energy, computed according to the initial awake-energy and according to awake-parameters computed for an awake-time interval based on output of sensor(s) comprising: a physiological sensor that senses a physiological parameter, and/or an activity sensor that senses an activity, and outputting, via a user interface, an indication of the current awake-energy, wherein the computing the current awake-energy and the outputting are dynamically iterated over the awake-time interval while the target individual is awake.

22 Claims, 10 Drawing Sheets

(51) Int. Cl.
| | |
|---|---|
| A63F 13/85 | (2014.01) |
| G09B 5/02 | (2006.01) |
| A63F 13/44 | (2014.01) |
| G09B 5/08 | (2006.01) |
| A63B 24/00 | (2006.01) |
| A61B 5/11 | (2006.01) |
| A61B 5/18 | (2006.01) |
| A61B 5/0205 | (2006.01) |
| G06T 11/20 | (2006.01) |
| G16H 20/00 | (2018.01) |
| A61B 5/0402 | (2006.01) |
| A61B 5/024 | (2006.01) |
| A61B 5/0476 | (2006.01) |
| A61B 5/145 | (2006.01) |
| A61B 5/08 | (2006.01) |
| A61B 5/0488 | (2006.01) |

(52) U.S. Cl.
CPC .............. *A63F 13/44* (2014.09); *A63F 13/85* (2014.09); *G06T 11/206* (2013.01); *G09B 5/02* (2013.01); *G09B 5/08* (2013.01); *G16H 20/00* (2018.01); *A61B 5/024* (2013.01); *A61B 5/0205* (2013.01); *A61B 5/0402* (2013.01); *A61B 5/0476* (2013.01); *A61B 5/0488* (2013.01); *A61B 5/0816* (2013.01); *A61B 5/14542* (2013.01); *A61B 2503/12* (2013.01); *G06T 2200/24* (2013.01)

(58) Field of Classification Search
CPC ........... A61B 5/163; A61B 5/168; A61B 5/18; A61B 5/11; A61B 5/1103; A61B 5/1118

USPC .................. 600/301, 544, 545, 558; 128/898
See application file for complete search history.

(56) References Cited

U.S. PATENT DOCUMENTS

| | | | | |
|---|---|---|---|---|
| 9,072,870 | B2* | 7/2015 | Wu | A61B 5/0031 |
| 10,010,253 | B2* | 7/2018 | Eyal | A61B 5/024 |
| 10,165,977 | B2* | 1/2019 | Wu | A61B 5/0031 |
| 10,504,617 | B2* | 12/2019 | Hattori | G16H 40/63 |
| 2006/0235315 | A1* | 10/2006 | Akselrod | A61B 5/02405 |
| | | | | 600/509 |
| 2009/0192556 | A1* | 7/2009 | Wu | A61B 5/0031 |
| | | | | 607/3 |
| 2016/0029890 | A1* | 2/2016 | Stump | A61B 5/0022 |
| | | | | 600/301 |
| 2016/0045141 | A1* | 2/2016 | Murakami | A61B 5/4809 |
| | | | | 73/491 |

OTHER PUBLICATIONS

Dworak et al., "Sleep and Brain Energy Levels ATP Changes during Sleep," The Journal of Neuroscience, Jun. 30, 2010 • 30(26): 9007-9016.*

Boostani et al., "2. A Comparative Review on Sleep Stage Classification Methods in Patients and healthy Individuals," 2016. hal-01390384.*

* cited by examiner

SYSTEMS AND METHODS FOR GENERATING A PRESENTATION OF AN ENERGY LEVEL BASED ON SLEEP AND DAILY ACTIVITY

BACKGROUND OF THE INVENTION

The present invention, in some embodiments thereof, relates to improving sleep and, more specifically, but not exclusively, to systems and methods for computing daytime energy levels based on sleep.

During sleep the human being is disconnected from the environment in different degrees and has a low degree of self-awareness. When awareness is returned upon wake up memories regarding sleep quality, quantity and duration are disturbed at different levels.

SUMMARY OF THE INVENTION

According to a first aspect, a computer implemented method of automatically creating a presentation of a current awake-energy level based on an analysis of sleep-parameters and awake-parameters for a target individual, the method comprises: computing an estimate of initial awake-energy at a wake-up time of the target individual according to a plurality of sleep-parameters computed according to a time interval that includes a previous night sleep of the target individual, computing an estimate of a current awake-energy of the target individual indicative of a remaining amount of an estimated maximal amount of available awake-energy, the current awake-energy computed according to the initial awake-energy and according to a plurality of awake-parameters computed for an awake-time interval of the target individual based on output of at least one sensor comprising one or both of: a physiological sensor that senses a physiological parameter of the target individual, and an activity sensor that senses an activity of the target individual, and outputting, via a user interface, an indication of the current awake-energy, wherein the computing the current awake-energy and the outputting are dynamically iterated over the awake-time interval while the target individual is awake.

According to a second aspect, a system for automatically monitoring for automatically creating a presentation of a current awake-energy level based on an analysis of sleep-parameters and awake-parameters for a target individual, the system comprises: a non-transitory memory having stored thereon a code for execution by at least one hardware processor of a computing device, the code comprising: code for computing an estimate of initial awake-energy at a wake-up time of the target individual according to a plurality of sleep-parameters computed according to a time interval that includes a previous night sleep of the target individual, code for computing an estimate of a current awake-energy of the target individual indicative of a remaining amount of an estimated maximal amount of available awake-energy, the current awake-energy computed according to the initial awake-energy and according to a plurality of awake-parameters computed for an awake-time interval of the target individual based on output of at least one sensor comprising one or both of: a physiological sensor that senses a physiological parameter of the target individual, and an activity sensor that senses an activity of the target individual, and code for outputting an indication of the current awake-energy, wherein the computing the current awake-energy and the outputting are dynamically iterated over the awake-time interval while the target individual is awake.

According to a third aspect, a computer program product for automatically creating a presentation of a current awake-energy level based on an analysis of sleep-parameters and awake-parameters for a target individual, the computer program product comprising: a non-transitory memory having stored thereon a code for execution by at least one hardware processor of a computing device, the code comprising: instructions for computing an estimate of initial awake-energy at a wake-up time of the target individual according to a plurality of sleep-parameters computed according to a time interval that includes a previous night sleep of the target individual, instructions for computing an estimate of a current awake-energy of the target individual indicative of a remaining amount of an estimated maximal amount of available awake-energy, the current awake-energy computed according to the initial awake-energy and according to a plurality of awake-parameters computed for an awake-time interval of the target individual based on output of at least one sensor comprising one or both of: a physiological sensor that senses a physiological parameter of the target individual, and an activity sensor that senses an activity of the target individual, and instructions for outputting an indication of the current awake-energy, wherein the computing the current awake-energy and the outputting are dynamically iterated over the awake-time interval while the target individual is awake.

At least some implementations of systems, methods, apparatus, and/or code instructions described herein relate to the technical problem of treating a target individual suffering from insufficient sleep. Insufficient sleep is a risk factor associated with a variety of medical conditions, for example, heart disease, heart attack, heart failure, irregular heartbeat, high blood pressure, stroke, diabetes, increased risk of accidents, and increased risk of sport injury. The technical problem may relate to incompliance of a target user with a recommended amount of sleep. The target user may intentionally deprive themselves of sleep, by sleeping for a short sleep duration that is less than the recommended amount of sleep. Such sleep deficiency results from voluntary insufficiency amount of sleep, and is not a result of a sleep-related problem such as insomnia.

At least some implementations of systems, methods, apparatus, and/or code instructions described herein relate to the technical problem of providing sleep therapy for behavioral sleep problems, for example, insomnia, excess caffeine intake during the day, excess exercise before going to sleep, and/or excess stress levels.

At least some implementations of systems, methods, apparatus, and/or code instructions described herein relate to the technical problem of motivating and/or encouraging users to sleep for longer time intervals.

At least some implementations of systems, methods, apparatus, and/or code instructions described herein relate to the technical problem of providing a feedback-mechanism to users that encourages obtaining sufficient sleep. The technical problem may relate to providing the users with incentives to increase sleep duration.

The technical problem may relate to how to indicate to a user his/her energy level in real time and/or as one or more historical values? Alternatively or additionally, the technical problem may relate to how to assist the user in performing an action based on the energy level, in an automatic manner?

The computed current awake-energy may provide an adherence persuasion tool to target individuals that intentionally deprive themselves of sufficient sleep. The quantification and/or visualization of the current awake-energy level may be used to persuade subjects with a low motivation to sleep of the importance of sleep, with the intent of increasing their sleep duration, which in turn increases daytime productivity and alertness by increasing the current awake-energy level throughout the day.

The computed current awake-energy may be integrated into a sleep therapy for behavior sleep problems of the target individual. The computed current awake-energy level may be used to mirror the target users' competency and/or capability of fulfilling daily obligations and/or activities in spite of low sleep satisfaction and/or perception. The quantification and/or visualization of the computed current awake-energy may help target users decrease anxiety levels around sleep, which is a big step towards improved sleep.

Some implementations of the systems, methods, apparatus, and/or code instructions described herein relate to the technical problem of adequately performing an activity that requires a certain amount of awake-energy for example, when the target subject has slept poorly. People who suffer from behavioral sleep problems tend to develop anxiety about falling asleep. One of the recurring worries is not being able to perform daily obligations due to poor sleep. The solution to the technical problem provided by some implementations of the systems, methods, apparatus, and/or code instructions described herein is based on identifying the activity, determining the amount of awake-energy required to perform the activity, determining whether the current awake-energy level of the user is sufficient to perform the activity, and outputting a recommendation for increasing the current awake-energy level to enable performing the activity when the current awake-energy level is insufficient for performing the activity.

In a further implementation form of the first, second, and third aspects, the plurality of sleep-parameters are selected from the group consisting of: total sleep time, sleep efficiency, arousal index, percent rapid eye movement (REM), percent deep sleep, sleep satisfaction, day time sleepiness, sleep quality, night stress, and sleep fragmentation.

In a further implementation form of the first, second, and third aspects, increasing values of the following sub-set of the plurality of sleep-parameters reduce the estimate of initial awake-energy: daytime sleepiness, arousal index, night stress, and sleep fragmentation.

In a further implementation form of the first, second, and third aspects, values of the following sub-set of the plurality of sleep-parameters within a range increase the estimate of initial awake-energy and values of the following sub-set of the plurality of sleep-parameters outside the range decrease the estimate of initial awake-energy:
percent REM, and percent deep sleep.

In a further implementation form of the first, second, and third aspects, the initial awake-energy is computed as a function that assigned a respective weight to each of the plurality of sleep-parameters, wherein each respective weight is computed for the target individual according to at least one of: an analysis of parameters of a plurality of previous sleeping intervals, and personal parameters of the target individual.

In a further implementation form of the first, second, and third aspects, the personal parameters of the target individual includes one or more members of the group consisting of: age, gender, optimal personal sleep duration determined according to an analysis of a population, medical conditions, and total estimated daytime activity of the user.

In a further implementation form of the first, second, and third aspects, the parameters of the plurality of previous sleeping intervals include one or more members of the group consisting of: total sleep time, sleep efficiency, arousal index, sleep satisfaction and daily nap time.

In a further implementation form of the first, second, and third aspects, the plurality of awake-parameters are based on a current time of the day.

In a further implementation form of the first, second, and third aspects, values of a sub-set of the plurality of awake-parameters within a range increase the current awake-energy and values of the sub-set of the plurality of sleep-parameters outside the range decrease the current awake-energy.

In a further implementation form of the first, second, and third aspects, the plurality of awake-parameters based on a current time of the day include an amount of time from the wake-up time, wherein the current awake-energy decays based on a decay-function from the initial awake-energy according to the amount of time from the wake-up time.

In a further implementation form of the first, second, and third aspects, the plurality of awake-parameters based on a current time of the day include an absolute current time, wherein the current awake-energy is according to circadian rhythm fluctuations according to the absolute current time.

In a further implementation form of the first, second, and third aspects, the plurality of awake-parameters based on a current time of the day are adjusted according to a profile of the target individual.

In a further implementation form of the first, second, and third aspects, the profile include at least one member of the group comprising: age, internal clock tendency, a genetic characteristic and at least one value indicative of the user condition during at least one previous nights.

In a further implementation form of the first, second, and third aspects, the plurality of awake-parameters are based on at least one of: an activity performed by the target individual and a current mental state of the target individual.

In a further implementation form of the first, second, and third aspects, the plurality of awake-parameters are selected from the group consisting of: daytime naps, caffeine consumption, alcohol intake, exercise, meals, stress level, result of reaction-time game, perception of energy state by the target individual, motivation, and mood.

In a further implementation form of the first, second, and third aspects, the estimate of initial awake-energy is computed according to an amount of time from when the target individual went to sleep and according to the awake-energy of the target individual when the target individual went to sleep.

In a further implementation form of the first, second, and third aspects, the indication presented within a GUI presented on a display of the user interface, a graphic of a battery that includes a bar graph, wherein the height of the bar graph of the battery is computed as the values of the current awake-energy as a percentage of the value of the estimate of the initial awake-energy, wherein the height of the bar graph is dynamically updated according to dynamic computations of the current awake-energy.

In a further implementation form of the first, second, and third aspects, the method further comprises and/or the system further comprises code instructions for and/or the computer program product further comprises additional instructions for predicting a future awake-energy of the target individual according to the estimate of initial awake-energy and a history of the current awake-energy, and outputting within the user interface the predicted future awake-energy for at least one future time interval.

In a further implementation form of the first, second, and third aspects, the method further comprises and/or the system further comprises code instructions for and/or the computer program product further comprises additional instructions for comparing the current awake-energy of the target individual to a recommended awake-energy of a demographically matched population of sample individuals.

In a further implementation form of the first, second, and third aspects, the method further comprises and/or the system further comprises code instructions for and/or the computer program product further comprises additional instructions for outputting at least one recommendation for increasing the current awake-energy to the recommended awake-energy when the current awake-energy is less than the recommended awake-energy.

In a further implementation form of the first, second, and third aspects, the method further comprises and/or the system further comprises code instructions for and/or the computer program product further comprises additional instructions for receiving an indication of a target activity for performance by the target individual, wherein the target activity is associated with a threshold energy value for proper execution of the target activity, comparing the current awake-energy of the target individual to the threshold energy value for proper execution of the target activity, and one or both of: when the current awake-energy is below the threshold outputting an indication of lack of sufficient current awake-energy to perform the target activity, and when the current awake-energy is above the threshold outputting an indication of sufficient current awake-energy to perform the target activity.

In a further implementation form of the first, second, and third aspects, the indication is at least one of: indicative of the target activity before execution, and indicative of the target activity during execution.

In a further implementation form of the first, second, and third aspects, the indication is for the target activity scheduled for a future time interval, and the comparing is executed between a predicted future awake-energy during the future time interval.

In a further implementation form of the first, second, and third aspects, the method further comprises and/or the system further comprises code instructions for and/or the computer program product further comprises additional instructions for outputting within the user interface, at least one recommendation for increasing the current awake-energy to the threshold energy value for proper execution of the target activity when the current awake-energy is less than the threshold energy value for proper execution of the target activity.

In a further implementation form of the first, second, and third aspects, the target activity is selected from the group comprising: driving a motor vehicle, exercise workout, decision make, and arguing.

In a further implementation form of the first, second, and third aspects, the method further comprises and/or the system further comprises code instructions for and/or the computer program product further comprises additional instructions for receiving from the user via the user interface, a manually entered estimate of the current awake-energy at a time interval, computing a difference between the manually entered estimate of the current awake-energy and the computed current awake-energy at the time interval, and outputting, via the user interface, an indication of the difference.

In a further implementation form of the first, second, and third aspects, the method further comprises and/or the system further comprises code instructions for and/or the computer program product further comprises additional instructions for presenting a reaction-time game on the user interface for estimate a reaction time of the target individual in response to at least one of a visual and auditory stimulus, computing at least one of the plurality of awake-parameters according to the reaction time, and dynamically updating the current awake-energy of the target individual according to the at least one of the plurality of awake-parameters computed according to the reaction time.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
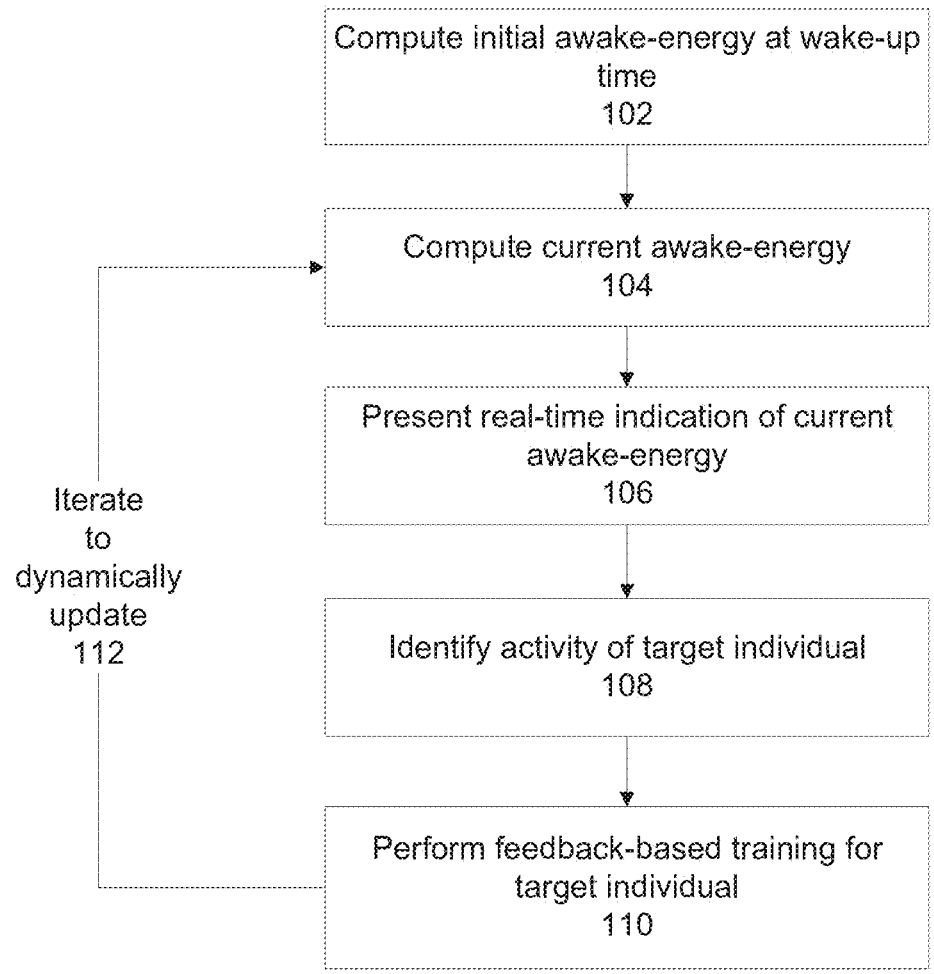
FIG. 1 is a flowchart of a method of automatically creating a presentation of current awake-energy level based on an analysis of sleep-parameters and awake-parameters for a target individual, in accordance with some embodiments of the present invention.

The present invention, in some embodiments thereof, relates to improving sleep and, more specifically, but not exclusively, to systems and methods for computing daytime energy levels based on sleep.

An aspect of some embodiments of the present invention relates to systems, methods, apparatus, and/or code instructions (i.e., stored in a data storage device executable by one or more hardware processors) for automatically creating a presentation, in real time and/or based on historical values of a current energy level status based on an analysis of sleep data (referred to herein as sleep-parameters) and user activity data (referred to herein as awake-parameters, for example, exercising, napping, working, and drinking coffee). An estimate of initial awake-energy at a wake-up time of the target individual is computed according to sleep-parameters, for example, computed based on manual user input, output of sensor(s), and/or data obtained from a dataset (e.g., electronic medical record).

The amount of initial awake-energy at wake-up time gradually declines as the day progresses and activities are performed, and/or may be increased at certain times of the day with certain other activities. The amount of initial awake-energy at the wake-up time does not necessarily represent the maximum amount of possible awake-energy available for the awake time (e.g., day), for example, due to insufficient sleep and/or disruptive sleep. The target individual may reach an energy level above the initial awake-energy, for example, by improving sleep habits and/or performing activities that increase the amount of available awake-energy (e.g., napping, drinking caffeinated drinks, and/or exercising). The sleep-parameters are computed according to a time interval that includes a previous night sleep of the target individual.

An estimated amount of a current awake-energy of the target individual is dynamically computed throughout the awake time (e.g., day), for example, continuously, at predefined time intervals, and/or triggered by events. The amount of computed current awake-energy, optionally in real-time, is indicative of the remaining amount of an estimated maximal amount of available awake-energy, optionally determined for the wake-up time. The maximal amount of available awake-energy may be estimated, for example, based on a previously obtained amount of awake-energy by the target individual, based on a previously obtained amount of awake-energy by other sample individuals that are similar to the target individual (e.g., in terms of demographics, medical profile, job type, and/or geographic location), and/or based on a mathematical model (e.g., equation(s)) that estimate the amount of sleep required for a certain individual based on a set of input parameters.

Conceptually, the current amount of awake-energy of the target individual represents the amount of charge left in the "battery" of the target individual. The "battery" receives an initial overnight charge by sleeping, to arrive at the amount of initial awake-energy at wake-up time. When the "battery" is charged properly by sufficient sleep, the amount of initial awake-energy at wake-up time matches the estimated maximal amount of available awake-energy, i.e., 100% charge. The "battery" does not match the estimated maximal amount of available awake-energy, when the "battery" is improperly charged, for example, by insufficient sleep and/or poor sleep. As the day progresses, the "battery" is discharged according to the time passed from the wake-up time (mainly discharged), and/or is discharged by certain activities (e.g., driving, working). The "battery" may be charged by other activities (e.g., napping, drinking coffee). It is noted that some activities may increase the battery for some users and decrease the battery for other users, for example, exercise. An indication as to the amount of charge of the "battery" aids the target individual in obtaining sufficient sleep, for example, in an effort to increase the amount of charge of the "battery" upon waking up.

The current awake-energy is computed relative to the estimated maximal amount of available awake-energy, for example, as a percentage. The current awake-energy is computed according to the initial awake-energy which serves as an initial amount of the current awake-energy that is adjusted as the day progresses according to awake-parameters computed for an awake-time interval of the target individual. The awake-parameters are computed based on output of a physiological sensor(s) that senses a physiological parameter of the target individual and/or an activity sensor(s) that senses an activity of the target individual. The awake-parameters may be computed based on input manually entered by the target individual, which may be measurable and/or perceived, for example, activities not detected by sensors (e.g., asking the user to manually indicate when caffeinated coffee is being drunk), and/or amount of current awake-energy perceived by the target individual. An indication of the estimated amount of current awake-energy is presented, in real-time and/or as historical data, for example, on a display (e.g., of a mobile device), within a graphical user interface (GUI), as a numerical percentage projected on a surface, and/or as an audio message played over speakers. The indication of the current awake-energy is dynamically updated throughout the awake time of the target individual (referred to herein as the awake-time interval).

Optionally, the real-time estimated amount of the current awake-energy determines whether an activity may be adequately performed by the target user. When the amount of energy required to adequately perform the activity is less than the real-time estimated amount of current awake-energy, an alert is generated indicating that the target user possess insufficient awake-energy to perform the activity, for example, as a message within the GUI, and/or as an audio message played over speakers. A recommendation for obtaining additional energy to perform the activity may be presented, for example, within the GUI, and/or as an audio message played over speakers.

At least some implementations of systems, methods, apparatus, and/or code instructions described herein relate to the technical problem of treating a target individual suffering from insufficient sleep. Insufficient sleep is a risk factor associated with a variety of medical conditions, for example, heart disease, heart attack, heart failure, irregular heartbeat, high blood pressure, stroke, diabetes, increased risk of accidents, and increased risk of sport injury. The technical problem may relate to incompliance of a target user with a recommended amount of sleep. The target user may intentionally deprive themselves of sleep, by sleeping for a short sleep duration that is less than the recommended amount of sleep. Such sleep deficiency results from voluntary insufficiency amount of sleep, and is not a result of a sleep-related problem such as insomnia.

At least some implementations of systems, methods, apparatus, and/or code instructions described herein relate to the technical problem of providing sleep therapy for behavioral sleep problems, for example, insomnia, excess caffeine intake during the day, excess exercise before going to sleep, and/or excess stress levels.

At least some implementations of systems, methods, apparatus, and/or code instructions described herein relate to the technical problem of motivating and/or encouraging users to sleep for longer time intervals.

At least some implementations of systems, methods, apparatus, and/or code instructions described herein relate to the technical problem of providing a feedback-mechanism to users that encourages obtaining sufficient sleep. The technical problem may relate to providing the users with incentives to increase sleep duration.

The technical problem may relate to how to indicate to a user his/her energy level in real time and/or as one or more historical values? Alternatively or additionally, the technical problem may relate to how to assist the user in performing an action based on the energy level, in an automatic manner?

The computed current awake-energy may provide an adherence persuasion tool to target individuals that intentionally deprive themselves of sufficient sleep. The quantification and/or visualization of the current awake-energy level may be used to persuade subjects with a low motivation to sleep of the importance of sleep, with the intent of increasing their sleep duration, which in turn increases daytime productivity and alertness by increasing the current awake-energy level throughout the day.

The computed current awake-energy may be integrated into a sleep therapy for behavior sleep problems of the target individual. The computed current awake-energy level may be used to mirror the target users' competency and/or capability of fulfilling daily obligations and/or activities in spite of low sleep satisfaction and/or perception. The quantification and/or visualization of the computed current awake-energy may help target users decrease anxiety levels around sleep, which is a big step towards improved sleep.

Some implementations of the systems, methods, apparatus, and/or code instructions described herein relate to the technical problem of adequately performing an activity that requires a certain amount of awake-energy for example, when the target subject has slept poorly. People who suffer from behavioral sleep problems tend to develop anxiety about falling asleep. One of the recurring worries is not being able to perform daily obligations due to poor sleep. The solution to the technical problem provided by some implementations of the systems, methods, apparatus, and/or code instructions described herein is based on identifying the activity, determining the amount of awake-energy required to perform the activity, determining whether the current awake-energy level of the user is sufficient to perform the activity, and outputting a recommendation for increasing the current awake-energy level to enable performing the activity when the current awake-energy level is insufficient for performing the activity.

The systems, methods, apparatus, and/or code instructions described herein do not simply perform automation of a manual procedure, but perform additional automated features which cannot be performed manually by a human using pencil and/or paper, for example, analysis of sensor output, creation of a presentation of current awake-energy level, and/or detection of activities being performed by the user. Moreover, as described herein, target users are unable to accurately evaluate their current awake-energy using subject and/or manual methods. Such users tend to statistically significant errors between their perceived current awake-energy levels and actual awake-energy levels. For example, target individuals tend to attribute much larger increases in awake-energy to drinking caffeinated beverages and greatly estimate the length of time that the increased awake-energy due to caffeine actually lasts. The automatically computed current awake-energy is unlike any computation a human may perform.

The systems, methods, apparatus, and/or code instructions described herein provide optionally real-time, optionally continuous, computing of the current awake-energy, detection of insufficient amount of current awake-energy to perform a desired activity (optionally in real-time), and/or predict a future amount of current awake-energy. An indication of the insufficient amount of current awake-energy to perform the desired activity may be presented on the GUI, optionally along with one or more suggestions to increase the current wake-energy above the threshold required to adequately perform the desired activity.

When the features related to by the systems, methods, apparatus, and/or code instructions described herein are taken as a whole, the combination of the features amounts to significantly more than a simple mathematical calculation of the current awake-energy. The systems, methods, apparatus, and/or code instructions described herein do not merely relate to mathematical computations (e.g., equations), but relate to the particular data collected, stored, and the way the data is collected by sensors and/or by the GUI, and optionally performing a prediction of future amount of current awake-energy and optionally whether the predicted future amount is sufficient to perform the desired activity.

At least some of the systems, methods, apparatus, and/or code instructions described herein improve an underling technical process within the technical field of sleep therapy, in particular, within the field of code instructions (e.g., applications loaded on a mobile device) that provide a user with self-help sleep therapy.

At least some of the systems, methods, apparatus, and/or code instructions described herein provide a unique, particular, and advanced GUI that provides a unique, particular, and advanced user experience that guides the target user towards increased awake-energy levels, for example, for performing one or more activities that require a certain minimum amount of awake-energy level.

At least some of the systems, methods, apparatus, and/or code instructions described herein generate new data in the form of the initial awake-energy and/or the current awake-energy of the target individual.

At least some of the systems, methods, apparatus, and/or code instructions described herein are tied to physical real-life components, for example, sensors that perform one or more measurements of parameters used to compute the initial awake-energy and/or the current awake-energy, physical data storage devices and/or memory, physical mobile devices, physical displays presenting the GUI, and/or physical hardware processors, to overcome an actual technical problem arising in sleep compliance of a target individual.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms user and target individual may sometimes be interchanged.

As used herein, the term presentation may refer to one or more presentation mechanisms, for example, a visual presentation on a display (e.g., within a GUI) and/or to an audio presentation (e.g., via speakers) and/or to a text presentation (e.g., on a device that presents text and/or numerical values).

As used herein, the general assumption is that people sleep at night and are awake during the day, however, the systems, methods, apparatus, and/or code instructions described herein are not necessarily limited to day and night, and are applicable to other scenarios where people are awake at night and sleep during the day (e.g., shift workers), are awake for extended periods of time that include night and day (e.g., on call physicians, soldiers, researchers in the arctic and/or Antarctica), and/or experience abnormal lengths of night and/or day (e.g., plane travelers).

Figure 2:
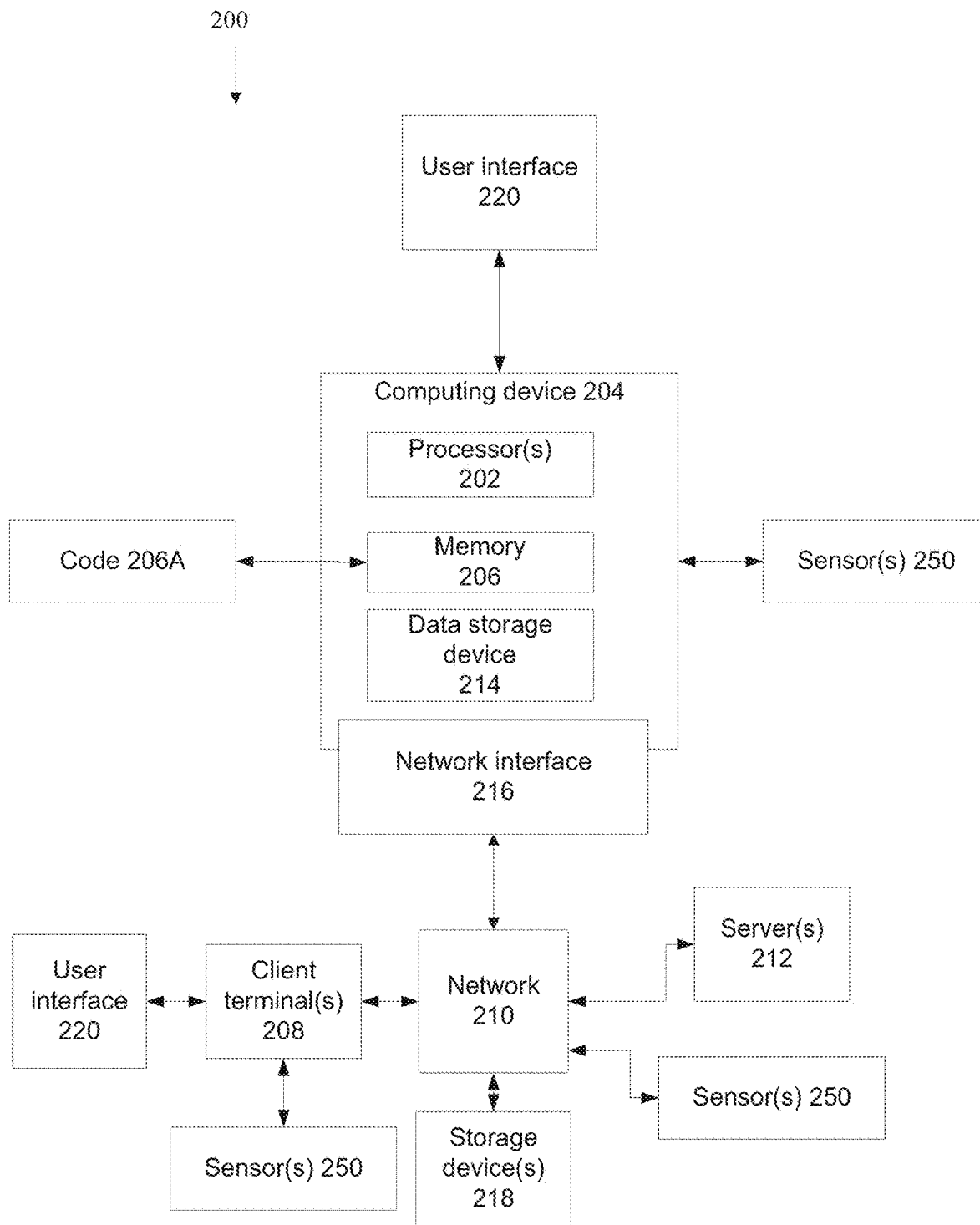
FIG. 2 is a block diagram of components of a system for automatically creating a presentation of current awake-energy level based on an analysis of sleep-parameters and awake-parameters for a target individual, in accordance with some embodiments of the present invention.

Reference is now made to FIG. 1, which is a flowchart of a method of automatically creating a presentation, optionally in real-time, of current awake-energy level based on an analysis of sleep-parameters and awake-parameters for a target individual, in accordance with some embodiments of the present invention. Reference is also made to FIG. 2, which is a block diagram of components of a system 200 for creating a presentation, optionally in real-time of current awake-energy level based on an analysis of sleep-parameters and awake-parameters, in accordance with some embodiments of the present invention. System 200 may implement the acts of the method described with reference to FIG. 1, by processor(s) 202 of a computing device 204 executing code instructions stored in a memory 206 (also referred to as a program store).

Daytime alertness and/or performance may depend on the sleep of one or more previous nights, in terms of, for example, sleep quality, duration, timing, and/or whether the target individual is habitually sleep deprived or whether sleep deprivation is a rare occurrence. The subject's energy level at wake up time and throughout the day, based on variables such as sleep quality, sleep duration and daily habits which influence alertness levels. The energy level is then quantified and visualized and is used as a tool to explain the importance of sleep.

Computing device 204 may be implemented as, for example, a client terminal, a server, a computing cloud, a virtual machine, a mobile device, a desktop computer, a thin client, a mobile device (e.g., a Smartphone, a Tablet computer, a laptop computer, a wearable computer, glasses computer, and a watch computer).

Multiple architectures of system 200 based on computing device 204 may be implemented. For example:

Computing device 204 may be implemented as a standalone device (e.g., kiosk, client terminal, smartphone) that include locally stored code instructions 206A that implement one or more of the acts described with reference to FIG. 1. The locally stored instructions may be obtained from another server, for example, by downloading the code over the network, and/or loading the code from a portable storage device.

Computing device 204 executing stored code instructions 206A, may be implemented as one or more servers (e.g., network server, web server, a computing cloud, a virtual server) that provides services (e.g., one or more of the acts described with reference to FIG. 1) to one or more client terminals 208 over a network 210. For example, providing software as a service (SaaS) to the client terminal(s) 208, providing software services accessible using a software interface (e.g., application programming interface (API), software development kit (SDK)), providing an application for local download to the client terminal(s) 208, providing an add-on to a web browser running on client terminal(s) 208, and/or providing functions using a remote access session to the client terminals 208, such as through a web browser executed by client terminal 208 accessing a web sited hosted by computing device 204.

Hardware processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include a single processor, or multiple processors (homogenous or heterogeneous) arranged for parallel processing, as clusters and/or as one or more multi core processing devices.

Memory 206 stores code instructions executable by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 206 stores code 206A that implements one or more features and/or acts of the method described with reference to FIG. 2 when executed by hardware processor(s) 202.

Computing device 204 may include a data storage device 214 for storing data, for example, awake-energy levels collected from a population of sample individual which serve as a reference for awake-energy levels of a target individual, awake-parameters and/or sleep-parameters of a single night/day and/or several nights/days or the target individual and/or of sample individuals, and local applications executed on computing device 204 that collect data for computing the awake-parameters for computation of the awake-energy (e.g., food application to track food/drink consumption, an exercise application to track exercise, a medical application to track medical problems, a calendar to track scheduled activities, and a diet application to track weight loss). Data storage device 214 may be implemented as, for example, a memory, a local hard-drive, virtual storage, a removable storage unit, an optical disk, a storage device, and/or as a remote server and/or computing cloud (e.g., accessed using a network connection).

Network 210 may be implemented as, for example, the internet, a local area network, a virtual network, a wireless network, a cellular network, a local bus, a point to point link (e.g., wired), and/or combinations of the aforementioned.

Computing device 204 and/or client terminal(s) 208 may be in communication with one or more sensor(s) 250 that perform measurements for collecting sleep-parameters and/or awake-parameters, as described herein in additional detail.

Computing device 204 may include a network interface 216 for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations.

It is noted that in the standalone implementation, network interface 216 is not necessarily required, as computing device 204 includes sensors 250 and/or user interface 220 in a single device that may operate without externally communication with other devices, for example, a smartphone, a kiosk, and a dedicated device.

Computing device 204 may connect using network 210 (or another communication channel, such as through a direct link (e.g., cable, wireless) and/or indirect link (e.g., via an intermediary computing unit such as a server, and/or via a storage device) with one or more of:

Remote server(s) 212 and/or storage devices 218 to access awake-energy levels from a population of sample individuals, and/or to upload new awake-energy data from the target individual to the dataset of the population.

Client terminal(s) 208, when computing device 204 is implemented as a server remotely providing the features and/or acts described with reference to FIG. 1.

Sensor(s) 250 that perform measurements for collecting sleep-parameters and/or awake-parameters.

Computing device 204 and/or client terminal(s) 208 include and/or are in communication with one or more physical user interfaces 220 that include a mechanism for a user to enter data (e.g., select GUI) and/or view the displayed results, within a GUI. Exemplary user interfaces 220 include, for example, one or more of, a touchscreen, a display, gesture activation devices, a keyboard, a mouse, and voice activated software using speakers and microphone.

Referring now back to FIG. 1, at 102, an estimate of initial awake-energy at a wake-up time of the target individual is computed. The estimate of initial awake-energy represents the initial values of the current awake-energy, for the target individual for the waking hours, determined at the time that the target individual wakes up from a night's sleep. The estimate of initial awake-energy is increased and/or decreased during the day according to the awake-parameters, as described herein.

The initial awake-energy may be represented as, for example, an absolute value in a certain unit, and/or a relative value. The relative value may be computed, for example, as one or more of the following:

The initial awake-energy is compared to the initial awake-energy of previous nights (e.g., via a sliding window of size 7 nights, or other sizes), and assigned as a percentage of the average of the average of the previous nights.

The initial awake-energy is compared to a potential amount of initial awake-energy representing the maximum possible amount of initial awake-energy the individual is capable of getting to, computed, for example, based on ideal sleep and/or based on the best sleep that may be realistically obtained.

The initial awake-energy of the target individual is compared to the initial awake-energy of a population of sample individuals, optionally corresponding to one or more personal profile parameters of the target individual, for example, in terms of age, weight, gender, medical conditions, geographic location, job type, and income.

The initial awake-energy of the target individual is compared to an estimated maximal possible amount of awake-energy computed based on a mathematical model of one or more equations, for example, that computes for a set of input parameters of the target individual (e.g., age, weight, gender, medical conditions, geographic location, job type, income) the estimated amount of required sleep for maximal awake-energy and/or computes the estimated amount of possible awake-energy.

Every initial awake-energy of each day is assigned a value of 100%, and the current awake-energy is computed relative to the 100%.

The estimate of initial awake-energy is computed as an aggregation of sleep-parameters. The sleep-parameters are computed according to a time interval that includes a previous night sleep of the target individual.

The sleep-parameters may be processed, for example, normalized, and/or converted into a common unit that provides for aggregation of the sleep-parameters into the initial awake-energy.

Sleep-parameters may be based on measurements and/or perceptions of the target individual indicative of perceived data. Measurements may be obtained from output of sensor(s) (e.g., physiological sensors, activity sensors) and/or may be obtained as data manually provided by the user via the physical user interface (e.g., via a GUI, gesture interface, and/or audio interface), for example, pressing an icon whenever caffeinated coffee is drunk. Perceptions of the target user may be obtained, for example, by the user manually entering data into the physical interface in response to one or more questions, for example, rate the quality of your sleep last night, how long did it take you to fall asleep, and how many times a night did you wake up. It is noted that the perceived data may be different than the measurements, for example, the user may perceive that it took 30 minutes to fall asleep, whereas a sensor may measure that it took the user 5 minutes to fall asleep.

Exemplary sleep-parameters include one or more of:

Total sleep time (e.g., measured in hours and/or minutes). Higher values contribute positively to increased amounts of initial awake-energy.

Sleep efficiency, denoting the ratio of the total time spend asleep (i.e., total sleep time) to the total amount dedicated to sleep (e.g., time spent in bed, including sleeping time and time trying to fall asleep, and/or time being awake after falling asleep). Higher values contribute positively to increased amounts of initial awake-energy.

Arousal index, denoting the total number of arousals (or short awakenings) divided by the total sleep time, and/or frequency of arousals (or short awakenings) events during the total sleep time. Higher values contribute to decreasing amounts of initial awake-energy. Lower values contribute to increased amounts of initial awake-energy.

Percent rapid eye movement (REM), denoting the percent of time during sleep spent in the REM state. Values of percent REM within a predefined range increase the estimate of initial awake-energy. Values of percent REM outside the range decrease the estimate of initial awake-energy.

Percent deep sleep, denoting the percent of time during sleep spent in the deep sleep state. Values of percent deep sleep within a predefined range increase the estimate of initial awake-energy. Values of percent deep sleep outside the range decrease the estimate of initial awake-energy.

Sleep satisfaction, denoting the perception of the target individual towards satisfaction from the night's sleep. Higher values contribute positively to increased amounts of initial awake-energy.

Day time sleepiness, denoting the perception of the target individual towards how tired/sleepy the user feels during the awake time. Higher values contribute to decreasing amounts of initial awake-energy. Lower values contribute to increased amounts of initial awake-energy.

Sleep quality, denoting the measured value of the target individual quality of the previous night's sleep. Sleep quality is computed as an aggregation of one or more measurements performed by one or more sensors that each measure a respective night parameter. The sleep quality is represented by a single value that grades the quality of sleep of the previous night. Higher values contribute positively to increased amounts of initial awake-energy.

Night stress, denoting the amount of stress the target individual experiences at night. Higher values contribute to decreasing amounts of initial awake-energy. Lower values contribute to increased amounts of initial awake-energy.

Sleep fragmentation, denoting the number of fragmentation events experienced by the target individual during the sleeping period (e.g., the night). Higher values contribute to decreasing amounts of initial awake-energy. Lower values contribute to increased amounts of initial awake-energy.

One or more sleep parameters may be automatically computed according to data of one or more sensors. Exemplary sensors include physiological sensors that measure one or physiological parameters of the target individual, and/or activity sensors that measure one or more activities of the target individual.

Exemplary activity sensors include: a microphone of the client terminal (e.g. smartphone) that senses noise such as snoring or lack or noise indicating sleep or senses the voice of the target individual indicating lack of sleep, a camera of the client terminal (e.g., smartphone) that capture images (e.g., video) of the target individual sleep and code that analyzes the images to compute the sleep-parameters, a location-based sensor (e.g., GPS) that senses the geographic location of the target individual, a mobility sensor that determines whether the target user is still (i.e., in bed sleeping or trying to sleep) or walking around, a bed-movement sensor that determined whether the target individual is lying still in bed or is moving around in bed (e.g., restless sleep, tossing and turning) such as an accelerometer.

Exemplary physiological sensors include: a heart rate sensor that measures heart rate, an eye state sensor that measures whether the eye is open or closed and/or eye movements, a breathing sensor that measures breathing rates, and a brain signal sensor that measures brain signals (e.g., EEG).

The output of the activity and/or physiological sensor(s) may be analyzed to identify when the target individual is sleeping, the state of sleep (e.g., REM, deep sleep, light sleep), when the target individual is awake, whether the target individual is in bed trying to sleep, and/or whether the target individual is experiencing high levels of stress. For example, sleep or awake states may be estimated according to heart rate, breathing rate, and brain signals. Total time trying to sleep may be estimated from output of the mobility sensor.

Sensors may be wearable, incorporated into an object worn by the target individual, for example, a watch, a necklace, a chest belt, a ring, socks, pants, shoes, undergarments, a wrist band, a head band, a smart shirt, a wall mounted sensor, and a hat. Exemplary wearable sensors include: a heart rate sensor that senses heart rate, a movement sensor that tracks steps (i.e., walking, running), an activity sensor that senses fitness activities, a calorie sensor that estimates calories being burnt, a temperature sensor that senses body temperature, a perspiration sensor that senses perspiration, a pulse oximeter that senses hemoglobin oxygenation levels, a breathing sensor that senses respiratory rate, and an electrogram sensor that measures electrical activity of tissue (e.g., heart, brain, and muscle).

Sensors may be contactless sensors that do not directly contact the target individual, for example, indirectly contacting the target individual, for example, located under the mattress, located on the surface of the mattress, and located within a bag and/or purse being carried by the target individual. Such sensors may be implemented, for example, as accelerometers, location based sensor, microphone, and/or camera of a Smartphone.

Sensors may be internet of things (IoT) enabled, which may be implemented within household items, for example, within a coffee machine to transmit indications of when the target individual user is drinking coffee, code that analyzes security surveillance videos to determine the location and/or activity of the target individual within the home, a smart-TV that transmits indications of when the target individual is watching television, and a IoT enabled treadmill that transmits indications of when the target individual is exercising.

One or more sleep parameters may be computed according to perceived data entered by the user via the GUI. For example, the target user marks on a scale (e.g., from 1 to 10) an indication of sleep satisfaction, day time sleepiness, and/or daytime stress.

Optionally, the initial awake-energy is computed as a function that assigned a respective weight to each of the sleep-parameters. Respective weights may computed for the target individual according to an analysis of parameters of one or more previous sleeping intervals (i.e., sleep over multiple previous nights). For example, a target individual that experiences stress over one isolated night is assigned a relatively low weight to the night stress parameter (since stress is not so significant for this target individual). Another target individual that experiences stress repeatedly over the last several nights is assigned a relatively high weight to the night stress parameter (since stress is very significantly impacting the ability of this other target individual to sleep properly). Alternatively or additionally, respective weights may computed for the target individual according to parameters computed for the one or more previous sleeping intervals and/or for one or more previous awake intervals, for example, average total sleep time, sleep efficiency, arousal index, sleep satisfaction, and daily nap time. Individuals that tend to have a high average total sleep time and/or tend to take daily naps may tolerate a night with reduced sleep.

Alternatively or additionally, respective weights may computed for the target individual according to personal parameters of the target individual, for example, age, medical condition, gender, occupation, total estimated daytime activity of the user geographical location, and optimal personal sleep duration. The personal parameters may be assigned weights according to the target individual in view of an analysis of a population of sample individuals. The data from the sample individuals may be uploaded from client terminals used by the sample individuals to a central server for aggregation and/or analysis. For example, a target user living in a cold climate may require more sleep according to sample individuals living in geographically similar regions, in comparison to other sample individuals living in warmer climates. In another example, a target user working in construction may require more sleep according to sample individuals working in similar professional, for example, in comparison to other sample individuals working in non-physical intensive occupations, for example, in an office.

Optionally, the estimate of initial awake-energy is computed according to an amount of time from when the target individual went to sleep and/or according to the awake-energy state of the target individual when the target individual went to sleep. The initial awake-energy may be computed based on parameter(s) determined before the target individual went to sleep. For example, including the time at which the target individual went to sleep, used to compute the total number of hours the target individual slept (according to when the target user woke up).

In another example, the initial awake-energy is affected by the amount of awake-energy at the time the target individual went to sleep. A certain target individual going to sleep very tired, which slept a full night, may experience less initial awake-energy in comparison to another target individual that went to sleep with more awake-energy and slept the same amount of time.

At 104, an estimate of a current awake-energy of the target individual is computed. The computing may be performed in real-time. The computing may be performed, for example, continuously (or at intervals which are statistically equivalent to continuous), at predefined intervals (e.g., every hour), and/or triggered by events (e.g., significant activities the user is performing).

The current awake-energy may be represented as, for example, an absolute value in a certain unit, and/or a relative value. The relative value may be computed, for example, as a percentage of the initial awake-energy which denotes the maximum amount of energy available for the day. The current awake-energy represents the amount of remaining energy from the estimated amount of maximal awake-energy.

The estimate of the current amount of awake-energy of the target individual is indicative of the remaining amount of the estimated amount of maximal awake-energy (e.g., representing the fully "charged battery"), and/or indicative of the remaining amount of the awake-energy from the initial awake-energy (e.g., representing the remaining amount of "charge" of the "battery" at wake-up time, which may be less than the maximal available awake-energy representing a fully "charged battery"). The decay may be computed according to awake-parameters.

The current awake-energy is computed according to awake-parameters computed for an awake-time interval of the target individual. The awake-time interval is the time that the target individual is awake for extended periods of time, and does not overlap with night sleep time. The awake-time interval may overlap with nap time, in which case the current awake-energy may increase due to the nap time when the target individual awakens from the nap. The awake-time interval does not include times during the night when the target individual is awake when the target individual should actually be sleeping, for example, due to difficulty falling asleep, insomnia, and stress.

The awake-parameters are computed based on output of one or more sensors as described herein (e.g., physiological sensors and/or activity sensors) and/or based on data manually entered by the user via the user interface.

The awake-parameters may be processed, for example, normalized, and/or converted into a common unit that provides for aggregation of the awake-parameters into the current awake-energy. The awake-parameters may be normalized and/or converted into the same unit used to represent the initial awake-energy.

Optionally, awake-parameter(s) are based on a current time of the day. The initial amount of awake-energy at wake-up time decays as the day progresses, optionally according to a monotonic decay pattern. The target individual gets progressively tired as the day passes by. The awake-parameters based on a current time of the day may include an amount of time from the wake-up time. The current awake-energy decays based on a decay-function from the initial awake-energy according to the amount of time from the wake-up time.

Alternatively or additionally, one or more awake-parameters may be computed as a function of the absolute time of the day. Alertness and/or awake-energy levels may fluctuate during the day. For example, during certain times of the day alertness and/or awake-energy decreases (i.e., feel more sleepy), and at other times of the day alertness and/or awake-energy increase (i.e., feel less sleepy). Values of a sub-set of the awake-parameters within a defined range increase the current awake-energy, and/or values of the sub-set of the sleep-parameters outside the defined range decrease the current awake-energy. The current awake-energy may be computed according to circadian rhythm fluctuations according to the absolute current time.

Optionally, the awake-parameters based on a current and/or absolute time of the day are adjusted according to a profile of the target individual. Exemplary profile parameters include: age, income, occupations, demographics, geographic location, medical conditions, medications, genetic characteristics, internal clock tendency (e.g., night owl or early bird), and/or condition of the target user during multiple previous nights.

The profile of the target individual may be created automatically, for example, by collecting and analyzing data, for example, the internal clock tendency of the target individual (e.g., whether the user is a night owl or early bird) may be determined by analyzing manually entered responses of the target individual to questions presented on the user interface. The profile of the target individual may be created based on the manually entered data, for example, a user providing answers to questions presented on the GUI and/or audio messages played on speakers, for example, how old are you? Are you a night owl or an early bird? It is noted that user tendencies (e.g., preferences) may be detected based on a questionnaire which indicates the theoretical preference of the target individual. The actual activity timing of the target individual does not necessarily match the theoretical tendency (e.g., internal clock) of the target individual. For example, the target individual may awake very early in the morning to get to work on time, but the ideal schedule preference of the target individual is to prefer to wake up much later in the day and stay awake at night.

The profile of the target individual may be created based on an analysis of a stored dataset (e.g., on a remote server), for example, medical data stored in an electronic medical record (EMR) of the target individual, and/or non-medical data stored in one or more non-medical datasets which may be associated with non-medical applications. The medical and/or non-medical data may be stored on server(s) accessed over the network. For example, certain medical conditions and/or use of certain medications extracted from the EMR suggest a higher sleep requirement. Examples of non-medical data include:

A food application stored data indicative the food that the target individual ate. The foods may be analyzed to identify healthy and/or caffeine consumption that increases awake-energy and/or unhealthy foods and/or heavy meals that lower awake-energy.

A sport application storing data indicative of exercise and/or fitness activities performed by the target individuals, for example, running, walking, dancing, mountain climbing, bike riding, and weight lifting. The exercise and/or fitness activities may be analyzed, for example, to identify moderate exercise and/or fitness activities that raise awake-energy levels, and/or intense exercise and/or fitness activities that lower awake-energy levels in the short term (i.e., the user is tired after performing them).

A diet application storing data indicative of weight loss by the target individual. Loss of weight may be associated with increased awake-energy levels.

The profile may include one value(s) indicative of the user condition during one or more previous nights, for example, does the target individual suffer from continuous sleep deprivation (e.g., based on the past predefined number of nights), or whether the target user slept according to computed sleep requirements of the target individual over the past predefined number of nights. Target individuals that are sleep deprived need assistance to catch-up on sleep and develop good sleeping habit. Target individuals that sleep according to computed requirements may tolerate a night of bad sleep. Exemplary profile parameters include total sleep time (TST) and total nap time (NAP).

Alternatively or additionally, one or more awake-parameters are based on an activity performed by the target individual and/or a current mental state of the target individual. Such awake-parameter may be computed, for example, according to outputs of one or more sensors (e.g., motion sensor indicating exercise, heart rate sensor indicating stress, and eye sensor indicating a nap), data extracted from a dataset (e.g., stored on a remote server, for example, EMR of the target individual), and/or collected from the target individual via the user interface (e.g., the target individual manually answering questions by speaking, gestures, and/or pressing a button on a display indicating the event occurring, for example, generating a meal diary). Exemplary awake-parameters based on an activity performed by the target individual and/or a current mental state of the target individual include:

Daytime naps. For example, the length of each nap, and time during the day of each nap.

Caffeine consumption. For example, the amount of caffeine ingested, and time during the day when each caffeine consumption occurred.

Alcohol intake. For example, the amount of alcohol ingested type of alcoholic beverage, and time during the day when each alcohol intake occurred.

Exercise. For example, the type of exercise, length of time of exercise, amount of calories burnt, and time during the day when exercise occurred.

Meals. For example, the amount of calories ingested, types of food eaten (e.g., food that give energy or foods that make one sleepy), and time during the day when each meal occurred.

Stress level. For example, an objective measure of stress (e.g., increased heart rate, increased breathing, increased perspiration) and/or a subjective measure of stress provided by the target individual. The intensity of stress, the length of time the stressful event lasts, and/or time of day of the stressful event.

Result of reaction-time game. The reaction-time game may be presented within the GUI, for example, at defined time intervals, at predefined events, and/or triggered by events, for example, after multiple activities have occurred. The reaction-time game measures a reaction time of the target individual in response to visual and/or auditory stimulus. For example, the user may be asked to press a button in the screen as fast as possible after hearing a certain sound, and/or after seeing a certain displayed image. A high score (e.g., short reaction time) may be indicative of relatively high awake-energy and/or alertness level. A low score (e.g., long reaction time) may be indicative of relatively low awake-energy and/or alertness level. One or more of the awake-parameters are computed according to the results of the reaction-time game. The current awake-energy of the target individual may be dynamically updated according to the awake-parameter(s) computed based on the measured reaction time.

Perception of energy state by the target individual. The target individual may manually indicate the perceived amount of awake-energy for example, at wake-up, and/or at one or more times throughout the day. The perceived amount of awake-energy may be entered at defined time intervals and/or at trigger events. The amount of perceived energy may be used to dynamically updated the computed amount of awake-energy, and/or trigger further analysis. For example, when the computed amount of awake-energy is statistically different from the perceived amount of energy entered by the user, additional sensor data may be analyzed and/or additional questions to the user may be presented to close the gap, for example, by correcting the computed amount of energy closer to the perceived energy, for example, when the computed awake-energy is less than the perceived energy, additional sensor measurements may be made to try and correct the computed awake-energy. Alternatively, the perceived energy is designated as incorrect and optionally an encouraging message is presented to the user, for example, "Your computed awake-energy is higher than you think! You have more energy than you think!".

Motivation. Optionally, a perception of motivation, which may be manually entered by the user via the user interface. The amount of motivation may be entered at defined time intervals and/or at trigger events.

Mood. Optionally, a perception of mood, which may be manually entered by the user via the user interface. The type of mood may be entered at defined time intervals and/or at trigger events.

When increasing values of sleep-parameters and/or awake-parameters increase the amount of awake-energy (i.e., initial and/or current) improved sleep and/or improved awake-energy are expected. The contribution of such parameters to the awake-energy is non-decreasing with increasing values of the respective parameter, for example, according to a sigmoid function, and/or other functions that include a combination of constant values and monotonic increasing variables.

When increasing values of sleep-parameters and/or awake-parameters decrease the amount of awake-energy (i.e., initial and/or current) reduced sleep and/or reduced awake-energy are expected. The contribution of such parameters to the awake-energy is non-decreasing with decreasing values of the respective parameter, for example, according to functions that include a combination of constant values and monotonic decreasing variables.

When values of certain sleep-parameters and/or awake-parameters are within predefined ranges (e.g., upper and lower thresholds), the contribution of such parameters to the amount of awake-energy (i.e., initial and/or current) may follow a "hill" type distribution, for example, a Gaussian, and/or a trapezoid, of the value of the parameters. It is noted that the distribution is not necessarily symmetric relative to the center of the maximal region.

When values of other certain sleep-parameters and/or awake-parameters are outside predefined ranges (e.g., upper and lower thresholds), the contribution of such parameters to the amount of awake-energy (i.e., initial and/or current) may follow a "valley" type distribution, for example, a parabola, of the value of the parameters. It is noted that the distribution is not necessarily symmetric relative to the center of the maximal region.

It is noted that parameters based on contribution of events as a function of time elapsed from occurrence of the event may be modeled as "hills" or "valleys".

At 106, an indication of the current awake-energy relative to the estimate of initial awake-energy is presented via the user interface, for example, within the GUI, displayed on a display, for example, of a Smartphone or other mobile device or other client terminal, and/or as audio played by speakers, for example, in response to a user saying the sentence "what is my energy level?".

Optionally, the indication is presented within the GUI as a graphic of a battery that includes a bar graph. The battery may be positioned within an image of a male or female, according to the personal profile of the target individual. The height of the bar graph of the battery corresponds to the value of the current awake-energy as a percentage of the value of the estimate of the initial awake-energy (i.e., current awake-energy divided by the initial awake-energy). The height of the bar graph is dynamically updated according to the dynamic computations of the current awake-energy.

Figure 3:
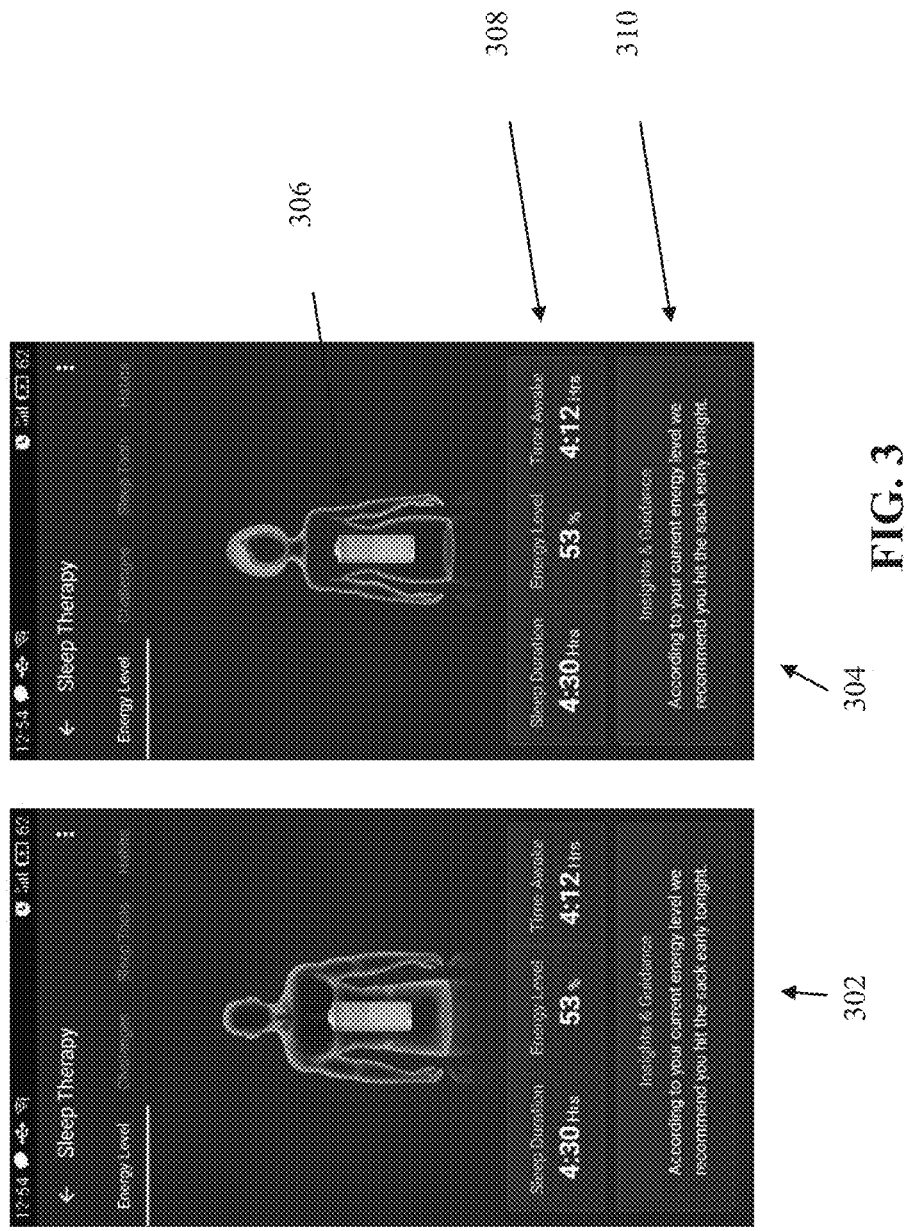
FIG. 3 is a schematic of a GUI presenting an indication of current awake-energy, in accordance with some embodiments of the present invention.

Reference is now made to FIG. 3, which is a schematic of a GUI presenting an indication of current awake-energy, in accordance with some embodiments of the present invention. GUI 302 may be presented for a male. GUI 304 may be presented for a female. GUI 302 and/or 304 include an image of a battery with a bar graph 306 having a height corresponding to the percent of current awake-energy in relation to the initial awake-energy during wake-up. GUI 302 and/or 304 may include one or more summary values 308, for example, the total sleep duration of the target patient during the previous night, current awake-energy level percent in numerical value (which is expressed in graphic form by bar graph of battery 306), and total time the target individual is awake since the wake-up time.

A personalized message and/or alert may be presented 310, for example, within a window. The message may be presented based on an analysis of the current awake-energy level, for example, in view of a history of awake-energy levels over the previous several days and/or in comparison to a population of sample individuals. For example, when the analysis indicates that the target individual has not slept enough, the following message may be displayed "According to your current energy level we recommend that you hit the sack early tonight."

Referring now back to act 106 of FIG. 1, optionally, a future awake-energy of the target individual is predicted according to the estimate of initial awake-energy and a history of the current awake-energy.

The prediction may be performed, for example, by a classifier (e.g., neural network) that analyzes historical trends of awake-energy. The prediction may be performed, for example, to estimate the amount of awake-energy of the target individual when a certain activity is planned (e.g., by accessing a calendar application on the client terminal) to determine whether the individual is predicted to have enough awake-energy to perform the planned activity. The prediction may be performed, for example, to estimate the amount of awake-energy of the target individual at an estimated bed-time, which may prompt an alert to the target individual to go to bed early due to a great lack of predicted awake-energy at the usual bed time. The prediction for the future time interval and/or future activity and/or the generated alert may be presented within the GUI.

Optionally, the current awake-energy of the target individual is compared to a recommended awake-energy of a matched population of sample individuals, for example, according to demographics, age, occupation, income, geographic region. When the awake-energy is below the recommended awake-energy, recommendation(s) for increasing the current awake-energy to the recommended awake-energy may be presented within the GUI. For example, as described with reference to alert 310 of FIG. 3.

Optionally, the GUI presents daily and/or weekly views of the awake-energy levels. Daily and/or weekly GUI views may reveal trends and/or insights into the target individual's sleep, habits, awake-energy patterns, and/or alertness fluctuations. Awake-energy levels may be compared to recommended values at certain time(s) of the day, based on the personal profile of the target individual and/or sample population, for example, as described herein.

The GUI may be automatically adjusted according to the gender of the target individual.

The GUI may present a real-time indication of the current awake-energy level, and/or at certain time intervals, for example, at noon, at dinner time, and/or throughout the day.

The GUI may include a trend line that indicates the decrease in the current awake-energy level from the initial awake-energy level, as the day progresses.

The GUI may include a graphical indication of activities and their effects on the awake-energy level, for example, by changes in the trend line and an icon, and/or tag indicating the activity. Exemplary activities that affect awake-energy levels include: caffeine consumption (increases awake-energy level), nap (increases awake-energy level), alcohol intake (decreases awake-energy level).

The weekly GUI view may provide a graphical comparison of awake-energy levels at corresponding times of different days of the week. The GUI may provide a graphical comparison of energy values from certain days and/or certain times.

Optionally, an alert is set according to a target requirement. The target requirement may be defined for one individual, and the alert transmitted to notify another individual, for example, transmitted as a message to a mobile device of the other individual. For example, parents are notified when their children's sleep duration is below the target requirement. In another example, one partner is notified when another partner's sleep and/or awake-energy level is below the target requirement. In yet another example, a healthcare provider is notified when an elderly and/or sick person's sleep and/or awake-energy level is below the target requirement.

At 108, an indication of a target activity for performance by the target individual is identified.

Figure 10:
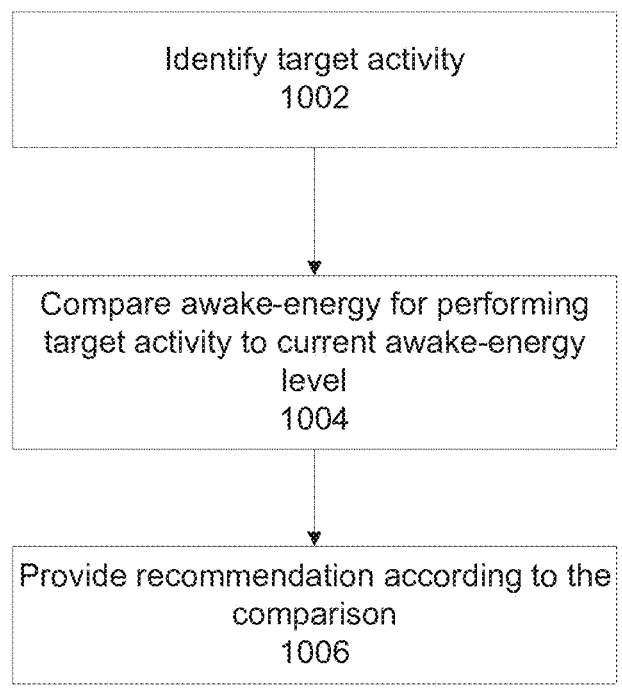
FIG. 10 is a flowchart of a method for analyzing a target activity of a target user according to an amount of available current awake-energy, in accordance with some embodiments of the present invention.

Reference is now made to FIG. 10, which is a flowchart of a method for analyzing a target activity of a target user according to an amount of available current awake-energy, in accordance with some embodiments of the present invention. The target activity is analyzed to determine whether the amount of current awake-energy of the target individual is sufficient for adequately performing the target activity by the target individual. When the amount of awake-energy is insufficient for performing the activity, one or more recommendations are presented within the GUI, for example, to increase the amount of available awake-energy to an amount sufficient for performing the activity.

As used herein, the term adequately performing refers to performing the target activity in a safe, alert, and normal manner, to obtain satisfactory results. For example, driving a car while tired greatly increases the risk of an accident and therefore the driving is not adequately performed. In another example, negotiating a large contract while tired may lead to errors and/or missing details, which may lead to a less than desired deal, and therefore the negotiating is not adequately performed. In another example, riding a bicycle while tired is unsafe due to inability to adequately monitor for motor vehicles.

At 1002, the target activity of the target individual is identified. Exemplary target activities include: driving a motor vehicle, exercise workout, decision making, arguing, performing, negotiating, scuba diving, taking a test, and making a big purchase. The target activity may be a currently executing activity, an impending activity that has not yet started, or a future scheduled activity. The activity may be automatically detected, for example, based on output of one or more sensors, and/or based on an analysis of one or more applications executing on the client terminal. The activity may be manually detected, for example, based on data entered manually by the user via the GUI.

The identified target activity may be currently executed, and detected by one or more sensors, for example, by a navigation application running on the smartphone (or other mobile device) that detects that the target individual is driving, by a microphone of the client terminal that detects that the voice of the target individual is at a higher volume and/or more rapid than usual indicating that the target individual is engaged in a debate and/or negotiation, by a mobility sensor (e.g., integrated within a smartwatch or smart wrist band) that detects that the target individual is performing a fitness activity (e.g., running, walking, riding a bike), and by code that accesses applications running on the client terminal that are in use (e.g., phone, calendar, word processing application).

The target activity may be impending but not yet executed, and detected, for example, by the target individual pressing an icon on the GUI indicating that the target activity is about to start, for example, an argument and/or negotiation.

The target activity may be scheduled for a future time interval, and detected for example, by analyzing a calendar application installed on the client terminal that extracts future scheduled activities.

At 1004, the energy value required to perform the identified target activity is compared to the awake-energy level.

Each target activity is associated with a respective threshold energy value indicative the minimum amount of awake-energy required for adequate execution of the target activity. The threshold may be stored, for example, in a database, and/or as a metadata tag of the activity. The threshold may be provided, for example, manually entered by a domain expert, automatically computed by code based on an analysis of previous activities performed by the target individual and how much awake-energy was required to adequately perform the activity, and/or based on an analysis of previous similar activities performed by a population of sample individuals (which may be matched, optionally demographically, to the target individual) and how much awake-energy was required to adequately perform the activity (e.g., average energy).

The current awake-energy of the target individual is compared to the threshold energy value for proper execution of the target activity.

Optionally, the target individual is asked to rate if the amount of current awake-energy was suitable for the activity, after the activity is performed by the target individual, for example, by manual user input entered via the user interface (e.g., GUI, display, audio input, gesture input). The feedback provided by the target individual is used to adjust the estimation of the required awake-energy to adequately perform future similar activities by the target individual and/or by other sample individuals.

At 1006, a recommendation is outputted according to the comparison of the energy required to perform the identified activity and the available awake-energy level, for example, presented within the GUI When the current awake-energy is below the threshold, an indication (e.g., message, audio sound, visual icon, text) of lack of sufficient current awake-energy to perform the target activity is generated. For example, when the current awake-energy is below the threshold for driving, a message indicating insufficient awake-energy for safe and alert driving is presented on the GUI, for example "Danger! Don't drive now! You are too tired".

When the current awake-energy is above the threshold, an indication of sufficient amount of awake-energy to perform the target activity is generated. For example, when the current awake-energy is above the threshold for driving, a message indicating sufficient awake-energy for safe and alert driving is presented on the GUI, for example "let's hit the road!".

Alternatively or additionally, recommendation(s) for increasing the current awake-energy to the threshold energy value for proper execution of the target activity is presented within the GUI when the current awake-energy is less than the threshold energy value for proper execution of the target activity. For example, the message "Drink 2 cups of coffee before driving" is presented. In another example, the message "Take a 30 minute power map before your big sales presentation this afternoon".

Alternatively or additionally, recommendation(s) for performing alternative activities are suggested. The alternative activities are associated with energy threshold levels that are below the current awake-energy level, and therefore are suitable for performance by the target individual. The alternatively activities may be in the same classification category at the target activity. For example, when the target individual would like to ride a bike for exercise, but has insufficient awake-energy, the substitute energy of going for a walk is recommended when the awake-energy of the target individual is sufficient for going for a walk.

Optionally, the results of the reaction-time game described herein (that uses measured reaction time to visual and/or auditory stimuli as indications of current awake-energy level and/or for computing awake-parameter(s)) may independently trigger a personalized message and/or alert. For example, when the measured reaction time is above a threshold for performing a certain activity, indicative that the user is less alert and/or has less awake-energy to perform the activity, an alert may be generated and presented within the GUI indicating to the target individual to refrain from the activity until the response time falls below the threshold.

Referring now back to FIG. 1, at 110, the target individual undergoes feedback-based training to improve perception of awake-energy levels and/or better understand fluctuations of awake-energy levels. The feedback-based training teaches the target individual about the cost and/or gain of different action, activities, and/or habits, for example, exercise, drinking coffee, and a nap.

The feedback-based training may be based on a game implemented within the GUI. The target individual is asked to guess their current awake-energy, in absolute value and/or in terms of percentage of the initial awake-energy level and/or in terms of percentage in comparison to other similar sample individuals (e.g., demographically matched). The target individual may be asked to guess the effect of the activity on the current awake-energy level, before and/or after the activity has occurred. For example, after the target user drank 2 cups of coffee, the target user is asked to guess how the coffee influenced the current awake-energy level in comparison to the pre-coffee awake-energy level. After a time interval has elapsed from the activity, the target individual may be asked (optionally again) to guess the current awake-energy level. The value entered by the target individual is compared to the computed current awake-energy level, and an appropriate message is presented. For example, an hour after the 2 cups of coffee, when the caffeine effect has decreased, the target individual is asked to enter the estimate of the awake-energy level. The target individual may learn that caffeine significantly increases the awake-energy level, but only for a limited time interval.

At 112, the computing the current awake-energy state and the presenting of the current awake-energy within the GUI are dynamically iterated while the target individual is awake.

Optionally, the initial awake-energy and/or current awake-energy values collected by the client terminal of the target individual are transmitted to a central server for analysis. The server receives the awake-energy values from multiple client terminals of multiple target individuals, and aggregates the data. The aggregate dataset may provide a reference for comparison of awake-energy values of the target individual in comparison to the sample population, optionally in comparison to a sub-set of the population that matches one or more personal profile parameters of the target individual, for example, by demographics. The initial awake-energy and/or current awake-energy of the target individual may be represented as a percentage of a reference amount of energy computed for the matched population. For example, a 75% initial awake-energy level indicates that the target individual wakes up with less energy in comparison to other similar sample individuals.

Reference is now made to FIGS. 4-9, which include exemplary GUIs depicting presentations of awake-energy levels and optionally summarize other aggregated data related to the awake-energy levels, in accordance with some embodiments of the present invention.

Figure 4:
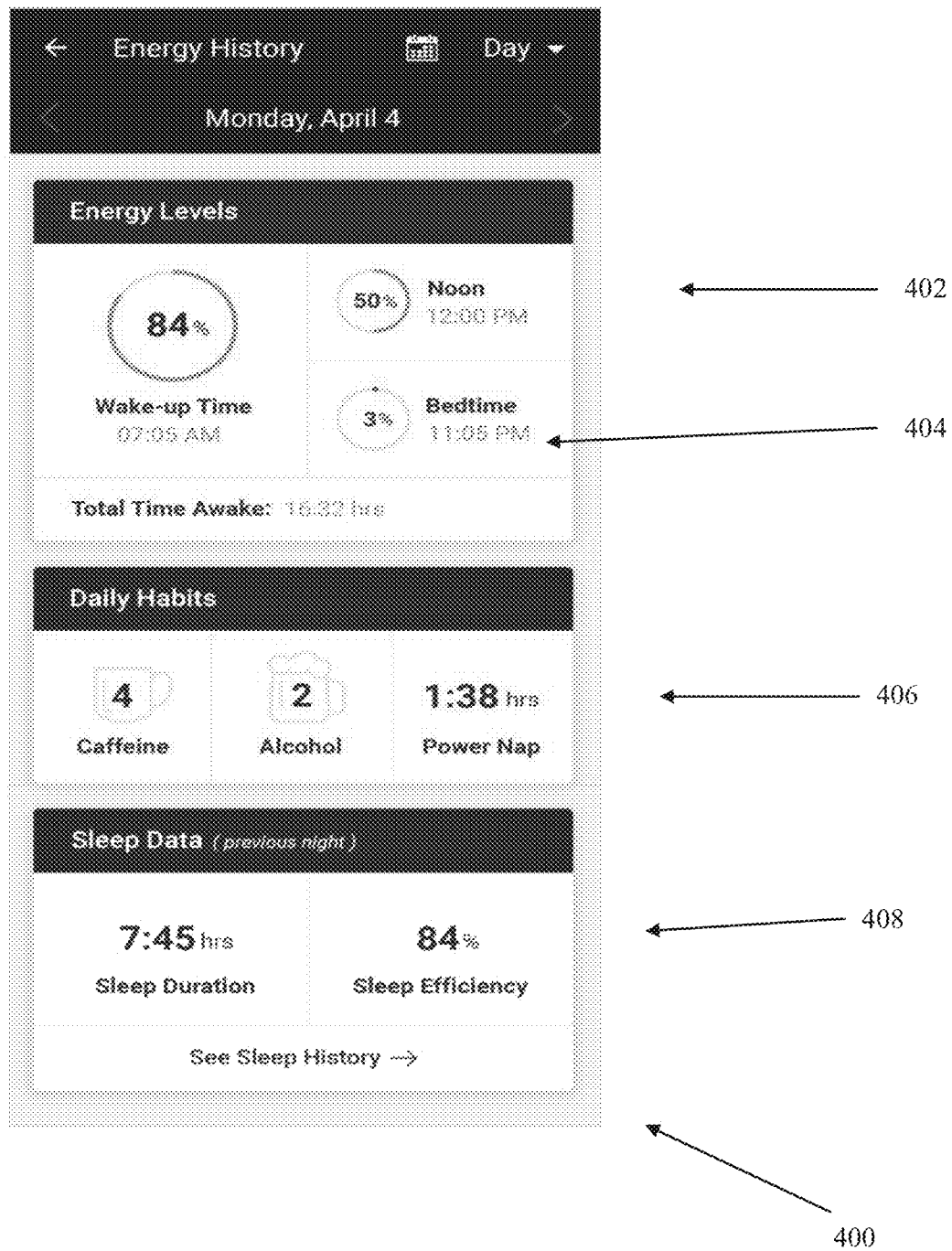
FIG. 4 is a GUI that presents a summary of awake-energy levels for a certain day, in accordance with some embodiments of the present invention.

Reference is now made to FIG. 4 depicts a GUI 400 that presents a summary of awake-energy levels for a certain day, in accordance with some embodiments of the present invention. The awake-energy levels are presented as a percentage of the initial awake-energy, and/or as a percentage of a computed maximum possible awake-energy. For example, the initial wake-up energy at wake-up time of 7:05 A is shown as 84%, where the 100% reference is computed based on a history of multiple previous initial awake-energy. The 84% may indicate that the target individual did not sleep well last in comparison to the average of multiple previous nights. Alternatively or additionally, the 100% reference is computed based on a population of sample individuals (e.g., demographically matched, and/or matched according to other personal profile parameters). Alternatively or additionally, the 100% reference is computed by a mathematical model. In such a case, the 84% indicates that the target individual wakes up with less energy than other sample individuals of the population and/or with less energy that is possible for the target individual to achieve.

An energy level window 404 displays awake-energy levels at key times of the day, for example, wake-up time, noon, and bedtime. A time counter may display the total time awake, taking into account nap times.

A daily habits window 406 displays a count, optionally in real-time, of significant activities that impact awake-energy levels, for example, number of cups of caffeinated coffee, number of alcoholic servings, and total time spent taking a power nap. The daily habits window may present a count, optionally in real-time, of significant activities performed today, and/or a summary of the current awake-energy level and count of significant activities performed in one or more previous days.

At sleep data window 408 displays a summary of the previous night's sleep, which impacted the initial awake-energy level. Window 408 may display values of one or more sleep parameters, optionally the sleep-parameters associated with greatest weight, and/or most significant sleep-parameters, for example, sleep duration, and sleep efficiency.

Figure 5:
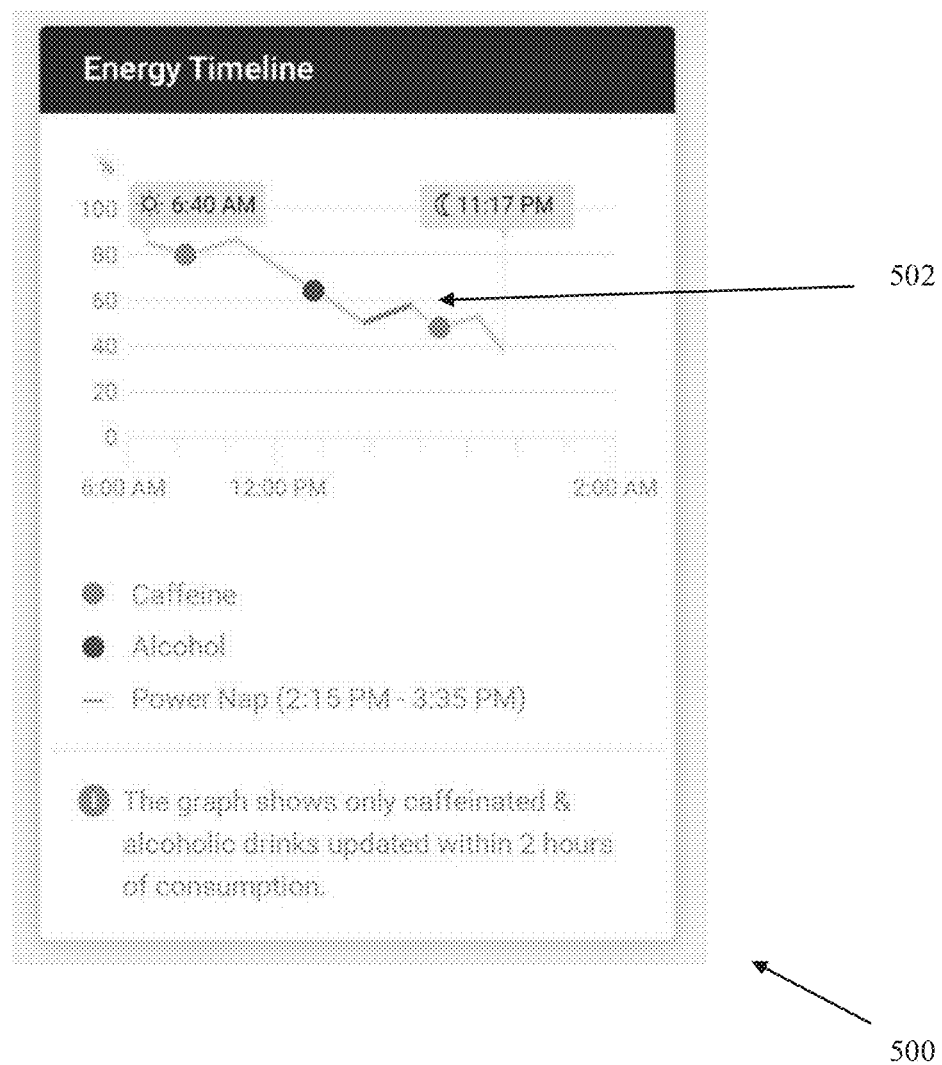
FIG. 5 is a GUI depicting a trend line indicating the awake-energy levels throughout the day, from wake-up to bed-time, in accordance with some embodiments of the present invention.

Reference is now made to FIG. 5, which is a GUI 500 depicting a trend line 502 indicating the awake-energy levels throughout the day, from wake-up to bed-time, in accordance with some embodiments of the present invention. The trend line is updated, in real-time and/or reflecting historic values, for example, continuously, at predefined intervals, and/or triggered by events (e.g., consumption of alcohol, caffeine, and/or taking a nap). The trend line provides a visual representation of fluctuations of the awake-energy levels during the day. Activities affecting awake-energy levels (e.g., consumption of alcohol, caffeine, and/or taking a nap) may be marked on the trend line, for example, using color coded icons. The effect of such activities on changes in awake-energy is visually represented by fluctuations of the trend line. For example, energy levels rise slightly after consumption of caffeine and a power nap, and fall after consumption of alcohol.

Figure 6:
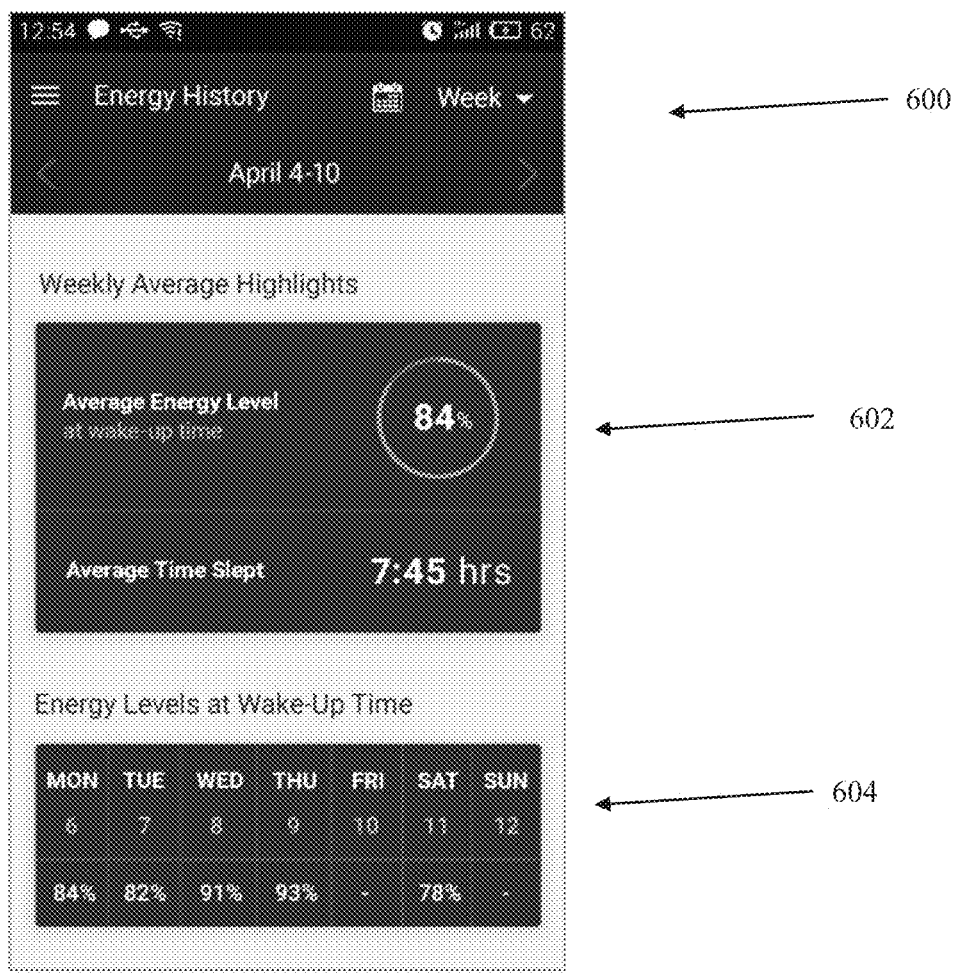
FIG. 6 is a GUI depicting weekly awake-energy levels, in accordance with some embodiments of the present invention.

Reference is now made to FIG. 6, which is a GUI 600 depicting weekly awake-energy levels, in accordance with some embodiments of the present invention. Window 602 display a summary of initial awake-energy levels for the week, and an average of time spent sleeping for the nights of the week. Window 604 presents a summary (e.g., in a table) of daily initial awake-energy levels for the week.

Figure 7:
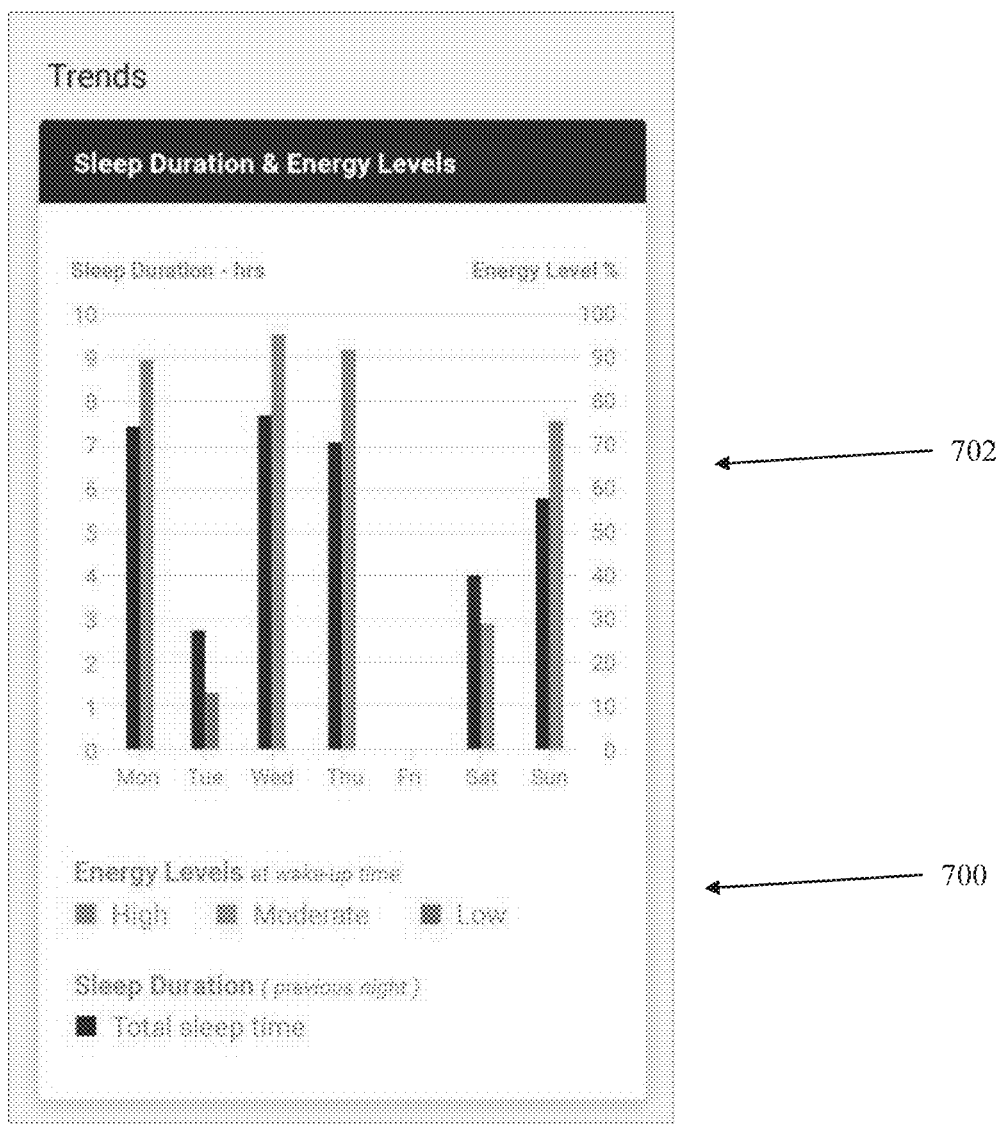
FIG. 7 is a GUI that graphically presents, for each day of the last week, a summary of total sleep time and associated initial awake-energy level, in accordance with some embodiments of the present invention.

Reference is now made to FIG. 7, which is a GUI 700 that includes a window 702 graphically presenting, for each day of a time interval window (e.g., the last week, early weeks, or other time intervals), a summary of total sleep time and associated initial awake-energy level, in accordance with some embodiments of the present invention. The total sleep time and associated initial awake-energy levels may be plotted as bar graphs, optionally color coded (e.g., according to a category of high, moderate, and low energy levels) which provide a visual indication of the correlation between sleep duration and initial awake-energy values.

Figure 8:
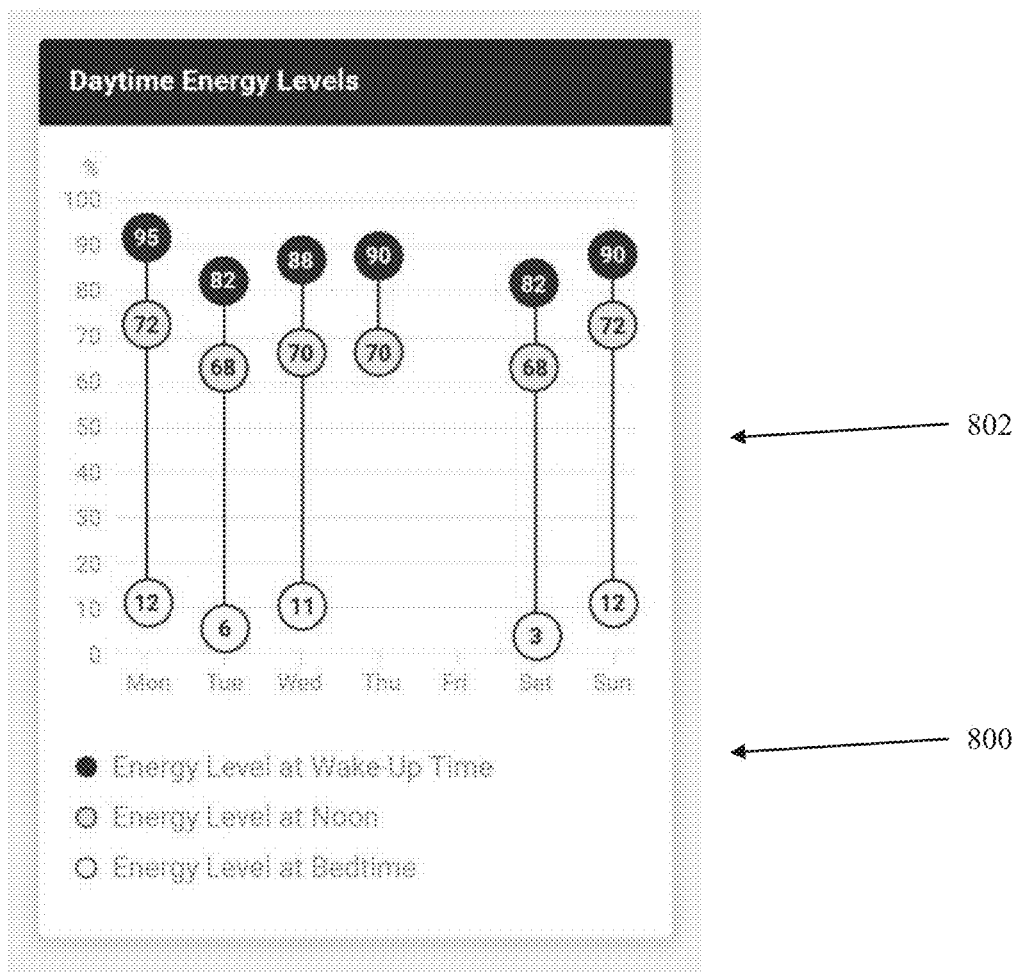
FIG. 8 is a GUI that graphically presents, for each day of the last week, a summary of the awake-energy level at wake-up time, at noon, and at bed-time, in accordance with some embodiments of the present invention.

Reference is now made to FIG. 8, which is a GUI 800 that includes a window 802 graphically presenting, for each day of the time window, a summary of the awake-energy level at wake-up time, at noon, and at bed-time, in accordance with some embodiments of the present invention.

Figure 9:
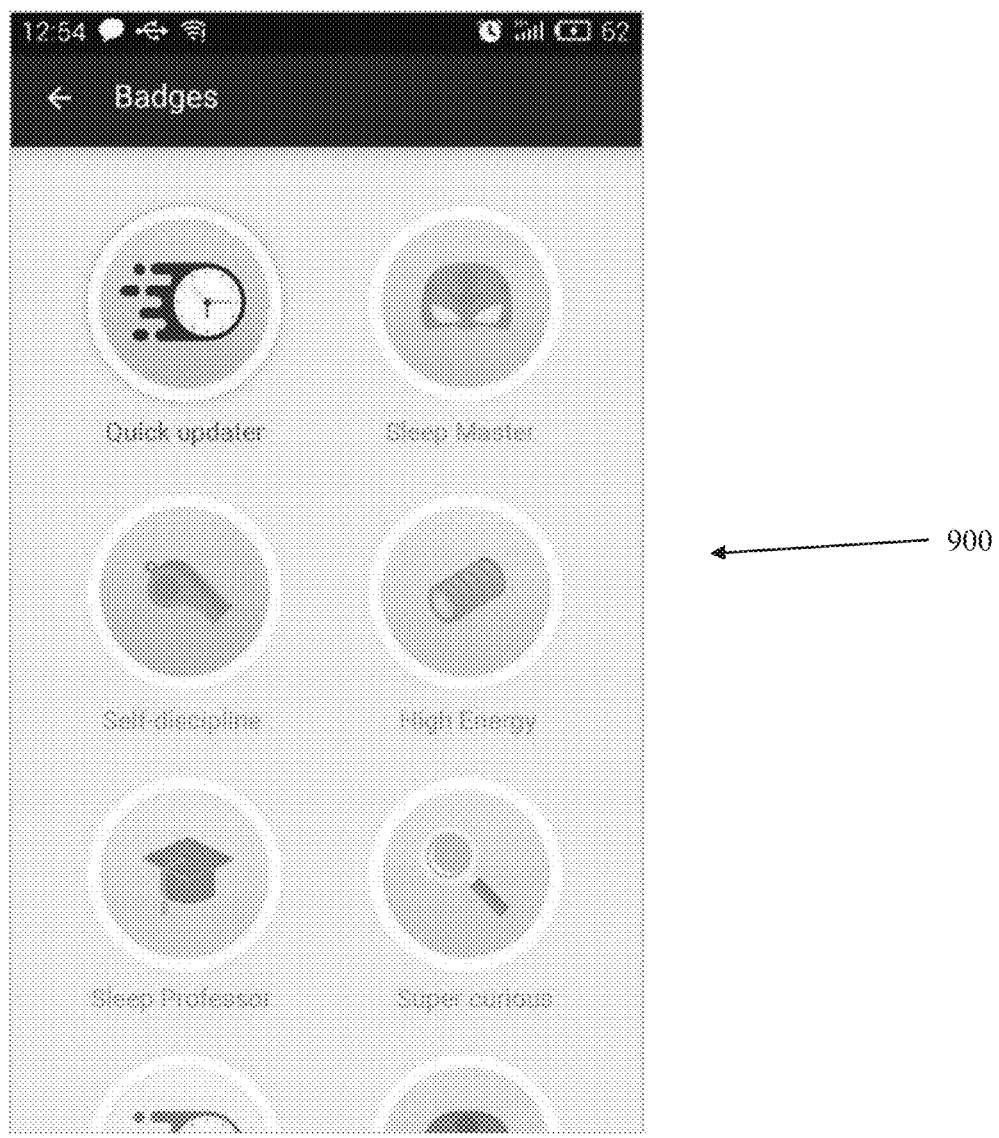
FIG. 9 is a GUI that depicts badge icons that are assigned according to the progress of the target individual towards reaching a personal set goal, and/or according to compliance with presented recommendations, in accordance with some embodiments of the present invention.

Reference is now made to FIG. 9, which is a GUI 900 that depicts badge icons that are assigned according to the progress of the target individual towards reaching a personal set goal, and/or according to compliance with presented recommendations, in accordance with some embodiments of the present invention. The goal and/or recommendations may include: increased sleep duration (e.g., sleeping at least 7 hours every night), reaching a target awake-energy level (e.g., waking up every day with an initial awake-energy level of at least 90%), improved daytime habits (e.g., reducing alcohol consumption), and avoidance of risky activities at low energy levels (e.g., driving).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant client terminals, and GUIs will be developed and the scope of the terms client terminal and GUI are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method of automatically creating a presentation of a current awake-energy level based on an analysis of sleep-parameters and awake-parameters for a target individual, the method comprising:

computing an estimate of initial awake-energy at a wake-up time of the target individual when the target individual woke up from a previous night sleep, the initial awake-energy computed according to a plurality of sleep-parameters computed during the time interval that includes the previous night sleep of the target individual, the plurality of sleep-parameters computed based on at least one of: an output of at least one sensor and data manually provided by a user;

initially setting an estimate of a current awake-energy of the target patient to the estimate of initial awake-energy, wherein the estimate of the current awake-energy is indicative of a remaining amount of the initial awake-energy;

dynamically adjusting, during an awake-time interval while the target individual is awake, the estimate of the current awake-energy of the target individual computed according to a plurality of awake-parameters computed for the awake-time interval of the target individual based on output of at least one sensor comprising one or both of: a physiological sensor that senses a physiological parameter of the target individual, and an activity sensor that senses an activity of the target individual; and outputting, via a user interface, an indication of the current awake-energy, wherein the dynamically adjusting, during an awake-time interval while the target individual is awake, the estimate of the current awake-energy and the outputting are dynamically iterated over the awake-time interval while the target individual is awake.

2. The method according to claim 1, wherein the plurality of sleep-parameters are selected from the group consisting of: total sleep time, sleep efficiency, arousal index, percent rapid eye movement (REM), percent deep sleep, sleep satisfaction, day time sleepiness, sleep quality, night stress, and sleep fragmentation.

3. The method according to claim 2, wherein increasing values of the following sub-set of the plurality of sleep-parameters reduce the estimate of initial awake-energy: daytime sleepiness, arousal index, night stress, and sleep fragmentation.

4. The method according to claim 2, wherein values of the following sub-set of the plurality of sleep-parameters within a range increase the estimate of initial awake-energy and values of the following sub-set of the plurality of sleep-parameters outside the range decrease the estimate of initial awake-energy: percent REM, and percent deep sleep.

5. The method according to claim 1, wherein the initial awake-energy is computed as a function that assigned a respective weight to each of the plurality of sleep-parameters, wherein each respective weight is computed for the target individual according to at least one of: an analysis of parameters of a plurality of previous sleeping intervals, and personal parameters of the target individual.

6. The method according to claim 5, wherein the personal parameters of the target individual includes one or more members of the group consisting of: age, gender, optimal personal sleep duration determined according to an analysis of a population, medical conditions, and total estimated daytime activity of the user.

7. The method according to claim 5, wherein the parameters of the plurality of previous sleeping intervals include one or more members of the group consisting of: total sleep time, sleep efficiency, arousal index, sleep satisfaction and daily nap time.

8. The method according to claim 1, wherein the plurality of awake-parameters are based on a current time of the day.

9. The method according to claim 8, wherein values of a sub-set of the plurality of awake-parameters within a range increase the current awake-energy and values of the sub-set of the plurality of awake parameters outside the range decrease the current awake-energy.

10. The method according to claim 8, wherein the plurality of awake-parameters based on a current time of the day include an amount of time from the wake-up time, wherein the current awake-energy decays based on a decay-function from the initial awake-energy according to the amount of time from the wake-up time.

11. The method according to claim 1, wherein estimate of initial awake-energy is computed according to an amount of time from when the target individual went to sleep and according to the awake-energy of the target individual when the target individual went to sleep.

12. The method according to claim 1, wherein the indication presented within a GUI presented on a display of the user interface, a graphic of a battery that includes a bar graph, wherein the height of the bar graph of the battery is computed as the values of the current awake-energy as a percentage of the value of the estimate of the initial awake-energy, wherein the height of the bar graph is dynamically updated according to dynamic computations of the current awake-energy.

13. The method according to claim 1, further comprising predicting a future awake-energy of the target individual according to the estimate of initial awake-energy and a history of the current awake-energy, and outputting within the user interface the predicted future awake-energy for at least one future time interval.

14. The method according to claim 1, further comprising:
comparing the current awake-energy of the target individual to a recommended awake-energy of a demographically matched population of sample individuals.

15. The method according to claim 14, further comprising:
outputting at least one recommendation for increasing the current awake-energy to the recommended awake-energy when the current awake-energy is less than the recommended awake-energy.

16. The method according to claim 1, further comprising:
receiving an indication of a target activity for performance by the target individual, wherein the target activity is associated with a threshold energy value for proper execution of the target activity;
comparing the current awake-energy of the target individual to the threshold energy value for proper execution of the target activity; and
one or both of: when the current awake-energy is below the threshold outputting an indication of lack of sufficient current awake-energy to perform the target activity, and when the current awake-energy is above the threshold outputting an indication of sufficient current awake-energy to perform the target activity.

17. The method according to claim 16, wherein the indication is at least one of: indicative of the target activity before execution, and indicative of the target activity during execution.

18. The method according to claim 16, wherein the indication is for the target activity scheduled for a future time interval, and the comparing is executed between a predicted future awake-energy during the future time interval.

19. The method according to claim 16, further comprising outputting within the user interface, at least one recommendation for increasing the current awake-energy to the threshold energy value for proper execution of the target activity when the current awake-energy is less than the threshold energy value for proper execution of the target activity.

20. The method according to claim 16, wherein the target activity is selected from the group comprising: driving a motor vehicle, exercise workout, decision make, and arguing.

21. The method according to claim 1, further comprising:
receiving from the user via the user interface, a manually entered estimate of the current awake-energy at a time interval;
computing a difference between the manually entered estimate of the current awake-energy and the adjusted current awake-energy at the time interval;
and outputting, via the user interface, an indication of the difference.

22. The method according to claim 1, further comprising:
presenting a reaction-time game on the user interface for estimate a reaction time of the target individual in response to at least one of a visual and auditory stimulus;
computing at least one of the plurality of awake-parameters according to the reaction time; and
dynamically updating the current awake-energy of the target individual according to the at least one of the plurality of awake-parameters computed according to the reaction time.

* * * * *